US008697643B2

(12) United States Patent
Lancaster et al.

(10) Patent No.: US 8,697,643 B2
(45) Date of Patent: Apr. 15, 2014

(54) METHOD FOR CONTROLLABLY RELEASING A DRUG CONJUGATE WITHIN SUBCUTANEOUS TISSUE IN RESPONSE TO THE LOCAL CONCENTRATION OF AN INDICATOR

(75) Inventors: Thomas M. Lancaster, Stoneham, MA (US); Matthew Nalewanski, Angleton, TX (US); Todd C. Zion, Marblehead, MA (US)

(73) Assignee: SmartCells, Inc., Beverly, MA (US)

( * ) Notice: Subject to any disclaimer, the term of this patent is extended or adjusted under 35 U.S.C. 154(b) by 123 days.

(21) Appl. No.: 13/366,744

(22) Filed: Feb. 6, 2012

(65) Prior Publication Data
US 2012/0135919 A1 May 31, 2012

Related U.S. Application Data

(62) Division of application No. 11/583,362, filed on Oct. 19, 2006, now abandoned.

(60) Provisional application No. 60/728,652, filed on Oct. 19, 2005.

(51) Int. Cl.
*A61K 38/28* (2006.01)
*A61P 3/10* (2006.01)
*A61K 9/10* (2006.01)

(52) U.S. Cl.
USPC .............. 514/5.9; 514/6.3; 514/6.9; 424/488

(58) Field of Classification Search
None
See application file for complete search history.

(56) References Cited

U.S. PATENT DOCUMENTS

| | | | |
|---|---|---|---|
| 4,002,531 A | 1/1977 | Royer | |
| 4,145,410 A | 3/1979 | Sears | |
| 4,348,387 A | 9/1982 | Brownlee et al. | |
| 4,766,106 A | 8/1988 | Katre et al. | |
| 5,284,934 A | 2/1994 | Allen | |
| 5,349,052 A | 9/1994 | Delgado et al. | |
| 5,583,144 A | 12/1996 | Kral | |
| 5,612,460 A | 3/1997 | Zalipsky | |
| 5,814,449 A | 9/1998 | Schultz et al. | |
| 5,830,506 A | 11/1998 | Taylor | |
| 5,902,603 A | 5/1999 | Chen et al. | |
| 5,902,607 A | 5/1999 | Taylor | |
| 6,063,116 A | 5/2000 | Kelleher | |
| 6,210,306 B1 | 4/2001 | Miller | |
| 6,267,002 B1 | 7/2001 | Ehwald et al. | |
| 6,410,053 B1 | 6/2002 | Taylor | |
| 6,413,494 B1 | 7/2002 | Lee et al. | |
| 6,454,710 B1 | 9/2002 | Ballerstadt et al. | |
| 6,477,891 B2 | 11/2002 | Ehwald et al. | |
| 6,671,527 B2 | 12/2003 | Petersson et al. | |
| 6,673,596 B1 | 1/2004 | Sayler et al. | |
| 6,938,463 B2 | 9/2005 | Ehwald et al. | |
| 7,259,139 B1 | 8/2007 | Kalinin et al. | |
| 7,531,191 B2 | 5/2009 | Zion et al. | |
| 2002/0054884 A1 | 5/2002 | Peetermans et al. | |
| 2002/0168409 A1 | 11/2002 | Taylor | |
| 2004/0043446 A1 | 3/2004 | De Frees et al. | |
| 2004/0202719 A1 | 10/2004 | Zion et al. | |

FOREIGN PATENT DOCUMENTS

| | | |
|---|---|---|
| EP | 0626862 B1 | 9/1999 |
| EP | 0706401 B1 | 11/2002 |
| WO | WO-93/13803 | 7/1993 |
| WO | WO-95/01186 | 1/1995 |
| WO | WO-95/06058 | 3/1995 |
| WO | WO-98/32466 | 7/1998 |
| WO | WO-2005/051987 | 6/2005 |

OTHER PUBLICATIONS

Agrawal et al., "Protein-Carbohydrate Interaction. XVIII. The Preparation and Properties of Acetylated Concanavalin A, the Hemagglutinin of the Jack Bean", *Biochemistry*, 7: 4211-18, 1968.
Allen et al., "Binding of Rat and Human Surfactant Proteins A and D to *Aspergillu fumigatus* Conidia", *Infection and Immunity*, 67(9): 4563-4569, 1999.
Armstrong et al., "Dextran-linked insulin: a soluble high molecular weight derivative with biological activity in vivo and in vitro", *Biochem. Biophys. Res. Commun.*, 47: 354, 1972.
Ballerstadt et al., "Competitive-binding assay method based of fluorescence quenching of ligands held in close proximity by a multivalent receptor", *Anal. Chim. Acta.*, 345: 203-12, 1997.
Baudys et al., "Extending Insulin Action in Vivo by Conjugation to Carboxymethyl Dextran", *Bioconjugate Chem.*, 9: 176-183, 1998.
Cheng, *Development of a Tissue Engineered Pancreatic Substitute Based on Genetically Engineered Cells*, Thesis, Georgia Institute of Technology, 2005.
De Jong, et al. "Physically Crosslinked Dextran Hydrogels by Stereocomplex Formation of Lactic Acid Oligomers: Degradation and Protein Release Behavior", *Journal of Controlled Release*, 71: 261-275, 2001.
Dillman et al., "Preclinical Trials with Combinations and Conjugates of T101 Monoclonal Antibody and Doxorubicin", *Cancer Research*, 46: 4886-4891, 1986.

(Continued)

*Primary Examiner* — Gyan Chandra
(74) *Attorney, Agent, or Firm* — John David Reilly; Immac J. Thampoe

(57) ABSTRACT

A conjugate that includes a drug covalently linked to a polymer. Upon administration, the conjugate is digested by an enzyme that is present at the site of administration thereby releasing a therapeutic agent. The conjugate may demonstrate substantially the same pharmacokinetic and pharmacodynamic behavior as the drug itself. A material for controllably releasing a conjugate in response to the local concentration of a molecular indicator. The material includes a plurality of conjugates and a plurality of multivalent cross-linking agents. The polymers of the conjugates include an analog of the indicator within their covalent structure. The multivalent cross-linking agents include cross-link receptors that interact with the indicator analog and thereby cross-link the conjugates. These non-covalent interactions are competitively disrupted when an amount of the molecular indicator is present thereby causing the material to release the conjugate in a manner that is dependent on the local concentration of indicator.

17 Claims, 13 Drawing Sheets

(56) References Cited

OTHER PUBLICATIONS

Dumestre-Perard et al., "Evaluation and Clinical Interest of Mannan Binding Lectin Function in Human Plasma", *Molecular Immunology*, 39: 465-473, 2002.

Eda et al., "Characterization of Truncated Human Mannan-Binding Protein (MBP) Expressed in *Escherichia coli*", *Biosci. Biotechnol. Biochem.*, 62(7): 1326-1331, 1998.

Eda et al., "Structure of a truncated human surfactant protein D is less effective in agglutinating bacteria than the native structure and fails to inhibit haemagglutination by influenza A virus", *Biochem J.*, 323:393-399, 1997.

Eda, et al., "Recombinant bovine conglutinin, lacking the N-terminal and collagenous domains, has less conglutination activity but is able to inhibit haemagglutination by influenza A virus", *Biochem J.*, 316:43-48, 1996.

Engel et al., "The Crystal Structure of Dipeptidyl Peptidase IV (CD26) Reveals is Functional Regulation and Enzymatic Mechanism", *PNAS*, 100(9): 5063-5068, 2003.

Gunther et al., "Concanavalin A Derivatives with Altered Biological Activities", *Proc. Natl. Acad. Sci. USA*, 70: 1012-6, 1973.

Halestrap et al., "The Proton Linked Monocarboxylate Transporter (MCT) Family: Structure, Function and Regulation", *Biochem. J.*, 343: 281-299, 1999.

Harada et al., "Determinants for the Drug Release from T-0128, Camptothecin Analogue-Carboxymethyl Dextran Conjugate", *Journal of Controlled Release*, 69: 399-412, 2000.

He, et al., *Life Sciences*, 65(4): 355-368, 1999.

Huynh et al., "Carboxymethylation of Dextran in Aqueous Alcohol as the First Step of the Preparation of Derivatized Dextrans", *Die Angewandte Makromolekulare Chemie*, 254: 61-65, 1998.

International Search Report for PCT/US06/41035, mailed Aug. 8, 2007.

International Search Report for PCT/US06/41167, mailed Oct. 19, 2006.

Johnson, et al., *J. of Bacteriology*, 91(3): 967-974, 1966.

Kagedal et al., "Binding of Covalent Proteins to Polysaccharides by Cyanogen Bromide and Organic Cyanates. I. Preparation of Soluble Glycine-, Insulin- and Ampicillin-Dextran", *Acta Chemica Scandinavica*, 25: 1855-1859, 1971.

Kim and Park "Glucose-binding property of pegylated concanavalin A", *Pharmaceutical Research*, 18: 794-99, 2001.

Kim and Park "Modulated insulin delivery from glucose-sensitive hydrogel dosage forms", *J. Controlled Release*, 77: 39, 2001.

Kim et al. "Insulinotropic activity of sulfonylurea/pullulan conjugate in rat islet microcapsule", *Biomaterials*, 24: 4843, 2003.

Looger et al., "Computational Design of Receptor and Sensor Proteins with Novel Functions", *Nature*, 423: 185-190, 2003.

Medina-Bolivar et al., "A non-toxic lectin for antigen delivery of plant-based mucosal vaccines", *Vaccine*, 21: 997-1005, 2003.

Mehvar et al., "Molecular-Weight-Dependent Pharmacokinetics of Fluorescein-Labeled Dextrans in Rats", *Journal of Pharmaceutical Sciences*, 81(9): 908-912, 1992.

Mislovicova et al., "Neoglycoconjugates of Mannan with Bovine Serum Albumin and Their Interaction with Lectin Concanavalin A", *Bioconjugate Chem.*, 13: 136-142, 2002.

Mitra et al., "Tumour Targeted Delivery of Encapsulated Dextran-Doxorubicin Conjugate Using Chitosan Nanoparticles as Carrier", *Journal of Controlled Release*, 74: 317-323, 2001.

Ohya et al., "Design of Macromolecular Prodrug of Cisplatin Using Dextran with Branched Galactose Units as Targeting Moieties to Hepatoma Cells", *Biomacromolecules*, 2: 927-933, 2001.

Persson et al., "Surfactant Protein D is a Divalent Cation-Dependent Carbohydrate-Binding Protein", *The Journal of Biological Chemistry*, 265(10): 5755-5760, 1990.

Sakamoto et al., "Comparative Effects of Native Insulin and Insulin-Dextran Complexes on the Metabolism of Adipose Tissue", *Biochimica et Biophysica Acta*, 498: 102-113, 1977.

Salins et al., "A Novel Reagentless Sensing System for Measuring Glucose Based on the Galactose/Glucose-Binding Protein", *Analytical Biochemistry*, 294: 19-26, 2001.

Sheriff et al., "Human Mannose-Binding Protein Carbohydrate Recognition Domain Trimerizes Through a Triple α-Helical Coiled-Coil", *Structural Biology*, 1(11): 789-794, 1994.

Sugahara et al., "Characteristics of Tissue Distribution of Various Polysaccharides as Drug Carriers: Influences of Molecular Weight and Anionic Charge on Tumor Targeting", *Biol. Pharm. Bull.*, 24(5): 535-543, 2001.

Suzuki et al., "Studies on the mode of insulin: properties and biological activity of an insulin-dextran complex", *Endocrinology*, 90: 1220-1230, 1972.

Tanna et al., "Covalent coupling of concanavalin A to a Carbopol 934P and 941P carrier in glucose-sensitive gels for delivery of insulin", *J. Pharm. Pharmacol.*, 11: 1461, 2002.

Thoma et al., "Versatile Functionalization of Polylysine: Synthesis, Characterization, and Use of Neoglycoconjugates", *J. Am. Chem. Soc.*, 121: 5919-5929, 1999.

Ueno et al., "Polyethylene Glycol-Modified Concanavalin A as an Effective Agent to Stimulate Anti-Tumor Cytotoxicity", *Cancer Detection and Prevention*, 24(1): 100-6, 2000.

Ueno et al., "Polyethylene glycol-modified pokeweed mitogen (PWM) as a potential non-immunogenic stimulator of lymphokine-activated killer cells", *J. Biomater. Sci. Polymer Edn.*, 7: 753, 1996.

Walsh, et al., Antimicrobal Agents and Chemotherapy, 47(2): 554-558, 2003.

Zion et al., "Bio-Inspired Nanoscale Hybrid Systems", *Materials Research Society*, Fall Meeting, Boston, MA, C10.12: p. 44, 55, Dec. 2-4, 2002.

Zion et al., "Glucose-responsive materials for self-regulated insulin delivery", Thesis, Massachusetts Institute of Technology, Dept. of Chemical Engineering, 2004.

METHOD FOR CONTROLLABLY RELEASING A DRUG CONJUGATE WITHIN SUBCUTANEOUS TISSUE IN RESPONSE TO THE LOCAL CONCENTRATION OF AN INDICATOR

PRIORITY INFORMATION

This application claims priority to U.S. Ser. No. 60/728,652 filed Oct. 19, 2005. The entire contents of this application are hereby incorporated by reference.

BACKGROUND OF THE INVENTION

The majority of "controlled-release" drug delivery systems known in the prior art (e.g., U.S. Pat. No. 4,145,410 to Sears which describes drug release from capsules which are enzymatically labile) are incapable of releasing drugs at intervals and concentrations which are in direct proportion to the amount of a molecular indicator (e.g., a metabolite) present in the human body. The delivery or release of drug in these prior art systems is thus not literally "controlled," but simply a slow release which is independent of external or internal factors.

The treatment of diabetes mellitus with injectable insulin is a well-known and studied example where uncontrolled, slow release of insulin is undesirable. In fact, it is apparent that the simple replacement of the hormone is not sufficient to prevent the pathological sequelae associated with this disease. The development of these sequelae is believed to reflect an inability to provide exogenous insulin proportional to varying blood glucose concentrations experienced by the patient. To solve this problem several biological and bioengineering approaches to develop a more physiological insulin delivery system have been suggested.

U.S. Pat. No. 4,348,387 to Brownlee et al. discloses a feedback controlled insulin delivery system wherein glucose-insulin conjugates are displaced by free glucose from binding sites on a glucose-binding molecule. The conjugated insulin retains its biological activity once released. In practical applications, however, the system is soluble and must be enclosed within a membrane that is permeable to glucose and glucose-insulin but not to the glucose-binding molecule. Without the use of a membrane or other external device to maintain a high local concentration of the glucose-binding molecule, the system dissociates at infinite dilution and releases the conjugate in a non-glucose dependent manner. Such a system that is not self-contained and requires the use of membranes is limited to use in extracorporeal or implantable devices and is not directly applicable to repeated administration, e.g., by injection. Furthermore, the system works well when confronted with short pulses of glucose such that the total amount of glucose introduced into the system is much less than the total amount of glucose-insulin bound to the glucose binding sites on the binding molecule. However, in the physiological milieu, molar glucose concentrations are approximately one million times higher than the concentration of insulin required to achieve a physiological effect. The net result is that when confronted with a critical glucose concentration in vivo, there is always enough glucose around to effectively displace and release all of the glucose-insulin from the system. Such a system is, therefore, incapable of responding to repeated glucose challenges in vivo, which is ultimately required for a closed-loop delivery system.

U.S. Pat. Nos. 5,830,506, 5,902,603, and 6,410,053 to Taylor et al. have attempted to address the lack of response to repeated glucose challenges. Instead of enclosing a soluble competitive binding system within a membrane, they have developed insoluble membranes based on competitive binding that control the rate of insulin release from a reservoir. As with the Brownlee system, Taylor's system is designed to be used in extracorporeal or implantable devices. The insoluble membrane is in the form of a gel that is formed by physically crosslinking water-soluble, glycosylated polymers with the tetravalent glucose-binding molecule concanavalin A (Con A). Free glucose enters the gel where it competes with the glycosylated polymer for Con A and disrupts the crosslinks, causing a gel-to-sol transition. Insulin that is physically trapped within the insoluble gel is thereby released. The gel is sandwiched between two porous support membranes to minimize leakage of the glycosylated polymer and Con A.

Taylor's system has two advantages over Brownlee's: (1) the device is reversible and therefore capable of responding to repeated glucose challenges and (2) the insulin does not require chemical modification. However, the use of support membranes ultimately leads to a complex system with slow diffusion rates. Consequently, excessively high glucose concentrations (>400 mg/dl) are required to significantly increase insulin diffusion. Furthermore, once glucose is removed from the system, the decrease in insulin release rate lags behind by several hours. The Taylor system is also severely limited because insulin release is not directly coupled to glucose concentration. Rather, insulin release is governed by diffusion through the glucose-responsive gel.

Zion et al. (U.S. Patent Application Publication No. 2004-0202719 and "Glucose-responsive materials for self-regulated insulin delivery", Thesis, Massachusetts Institute of Technology, Dept. of Chemical Engineering, 2004) address the lack of response to repeated glucose challenges in a different manner than Taylor. In certain embodiments of their system, they combine a multivalent glucose-binding molecule with a glycosylated polymer-insulin conjugate. The glycosylated polymer contains multiple saccharide binding groups and forms insoluble hydrogels or particles in the presence of the glucose-binding molecule. In the Brownlee system, the glucose-insulin conjugate was not polymeric and only contained one saccharide binding group per insulin molecule, which was not sufficient to form a cross-linked, insoluble system. In the Taylor system, the insulin is physically immobilized within the gel instead of being associated with a glycosylated polymer. Zion et al. also describe uses of their system for the controlled delivery of drugs other than insulin. These systems are responsive to the same or a different molecular indicator that is present within the body.

Because the Zion system is insoluble, it is self-contained and does not require the use of membranes to function, making it suitable for repeated dosing, e.g., through injection. Zion et al. have also demonstrated that the rate of dissolution in their system, and therefore the rate of polymer-drug release, is proportional to the local concentration of the indicator molecule. Finally, because the material dissolves from the outside inward rather than volumetrically, the material is capable of responding to repeated challenges, unlike the Brownlee system.

The Zion system is also superior to Taylor's because the drug is covalently linked to the polymer rather than physically immobilized in the system. As a result, precise control can be obtained over the dose and rate of delivery even for very small changes in concentration of the indicator molecule within the physiological range. For example, where Taylor et al. demonstrate a two- to four-fold increase in insulin release rate from 0 to 1,000 mg/dl glucose, Zion et al. have demonstrated a 50 fold increase in insulin release rate from just 50 to 400 mg/dl glucose.

Whether used to deliver insulin or other drugs, the Zion system suffers from one disadvantage. Indeed, the polymer-drug conjugate that is released has a higher molecular weight (MW) than the unmodified insulin of Taylor or the glucose-insulin conjugate of Brownlee. The conjugate is therefore absorbed into the systemic circulation much more slowly. In addition, once in the circulation, the intrinsic bioactivity of the polymer-drug is diminished and the rate of elimination is slower. Therefore, there is a need in the art for a stimuli-responsive drug delivery system constructed from a crosslinking molecule and a polymer-drug in which the polymer-drug acts as rapidly and to the same extent as the unmodified drug. Advantageously, this new polymer-drug could itself also be used as a delivery device, i.e., without being included within a stimuli-responsive drug delivery system.

SUMMARY OF THE INVENTION

In one aspect, the invention provides a conjugate that includes a drug covalently linked to a polymer. The polymer and drug can be directly linked or indirectly linked through a spacer. Upon administration, the conjugate is digested by an enzyme that is present at the site of administration thereby releasing a therapeutic agent, e.g., the drug itself or the drug and a portion of the polymer or spacer. In one embodiment the conjugate is designed for subcutaneous administration. In one embodiment, the polymer is susceptible to digestion by the enzyme. In other embodiments, the spacer is susceptible to digestion by the enzyme. In one embodiment, the rate of digestion at the site of administration is such that the conjugate demonstrates substantially the same pharmacokinetic and pharmacodynamic behavior as the drug itself.

In another aspect, the invention provides a material for controllably releasing a conjugate in response to the local concentration of a molecular indicator. The material includes a plurality of conjugates and a plurality of multivalent cross-linking agents. The polymers of the conjugates include an analog of the indicator within their covalent structure. The multivalent cross-linking agents include cross-link receptors that interact with the indicator analog and thereby cross-link the conjugates. These non-covalent interactions are competitively disrupted when an amount of the molecular indicator is present thereby causing the material to release the conjugate in a manner that is dependent on the local concentration of indicator.

The invention also provides methods of making and using the conjugate, methods of making and using a material that controllably releases a conjugate, and kits that include the conjugate and other reagents for preparing a material that controllably releases a conjugate.

Definitions

"Antigenic": As used herein, the term "antigenic" refers to the ability of a substance to produce antibodies when introduced into the body. Antigenicity is a measure of the capacity for a particular compound to produce antibodies. Antigenicity is generally measured as a minimum concentration of a substance to produce a statistically significant increase in antibody levels and/or the level of antibodies produced at a given concentration for a particular immunization protocol.

"Biomolecule": As used herein the term "biomolecule" refers to molecules (e.g., proteins, amino acids, peptides, polynucleotides, nucleotides, carbohydrates, sugars, lipids, nucleoproteins, glycoproteins, lipoproteins, steroids, etc.) whether naturally-occurring or artificially created (e.g., by synthetic or recombinant methods) that are commonly found in cells and tissues. Specific classes of biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA, and RNA.

"Biocompatible": As used herein, "biocompatible" materials and solutions are materials and solutions that do not elicit an undesirable detrimental response in vivo.

"Drug": As used herein, the term "drug" refers to small molecules or biomolecules that alter, inhibit, activate, or otherwise affect biological or chemical events. For example, drugs may include, but are not limited to, anti-AIDS substances, anti-cancer substances, antibiotics, anti-diabetic substances, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anti-coagulants and/or anti-thrombotic agents, local anesthetics, ophthalmics, prostaglandins, anti-depressants, anti-psychotic substances, anti-emetics, and imaging agents. A more complete listing of exemplary drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", edited by Susan Budavari et al., CRC Press, 1996, and the United States Pharmacopeia-25/National Formulary-20, published by the United States Pharmcopeial Convention, Inc., Rockville Md., 2001.

"Enzyme": As used herein, the term "enzyme" is used to refer to any of numerous proteins or conjugated proteins produced by living organisms that function as biochemical catalysts. Enzymes capable of catalyzing the hydrolytic cleavage of particular polymers or specific chemical bonds are of particular interest for this specific application. Examples of enzyme families include saccharidases that are capable of cleaving polysaccharide linkages, peptidases that are capable of cleaving polypeptide linkages, and nucleases that are capable of cleaving polynucleotide linkages.

"Growth Factors": As used herein, "growth factors" are chemicals that regulate cellular metabolic processes, including but not limited to differentiation, proliferation, synthesis of various cellular products, and other metabolic activities. Growth factors may include several families of chemicals, including but not limited to cytokines, eicosanoids, and differentiation factors.

"Polymer": As used herein, a "polymer" is a compound that includes a string of covalently linked monomers. A polymer can be made from one type of monomer or more than one type of monomer. The term "polymer" therefore encompasses copolymers, including block-copolymers in which different types of monomer are grouped separately within the overall polymer. A polymer can be linear or branched.

"Polynucleotide": As used herein, a "polynucleotide" is a polymer of nucleotides. The terms "polynucleotide", "nucleic acid", and "oligonucleotide" may be used interchangeably. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, 4-acetylcytidine, 5-(carboxyhydroxymethyl) uridine, dihydrouridine, methylpseudouridine, 1-methyl adenosine, 1-methyl guanosine, N6-methyl adenosine, and 2-thiocytidine), chemically modified bases, biologically modified bases (e.g., methylated bases), intercalated bases, modified sugars (e.g., 2'-fluororibose, ribose, 2'-deoxyribose, 2'-O-methylcytidine, arabinose, and hexose), or modified phosphate groups (e.g., phosphorothioates and 5'-N-phosphoramidite linkages).

"Polypeptide": As used herein, a "polypeptide" is a polymer of amino acids. The terms "polypeptide", "protein", "oligopeptide", and "peptide" may be used interchangeably. Polypeptides may contain natural amino acids, non-natural amino acids (i.e., compounds that do not occur in nature but that can be incorporated into a polypeptide chain) and/or amino acid analogs as are known in the art. Also, one or more of the amino acid residues in a polypeptide may be modified, for example, by the addition of a chemical entity such as a carbohydrate group, a phosphate group, a farnesyl group, an isofarnesyl group, a fatty acid group, a linker for conjugation, functionalization, or other modification, etc. These modifications may include cyclization of the peptide, the incorporation of D-amino acids, etc.

"Polysaccharide": As used herein, a "polysaccharide" is a polymer of sugars. The terms "polysaccharide", "carbohydrate", and "oligosaccharide", may be used interchangeably. The polymer may include natural sugars (e.g., glucose, fructose, galactose, mannose, arabinose, ribose, and xylose) and/or modified sugars (e.g., 2'-fluororibose, 2'-deoxyribose, and hexose).

"Saccharide": As used herein, the term "saccharide" refers to monomers of sugars. A saccharide can be a natural sugar (e.g., glucose, fructose, galactose, mannose, arabinose, ribose, and xylose) or a modified sugar (e.g., 2'-fluororibose, 2'-deoxyribose, hexose, etc.).

"Small molecule": As used herein, the term "small molecule" refers to molecules, whether naturally-occurring or artificially created (e.g., via chemical synthesis), that have a relatively low molecular weight. Typically, small molecules are monomeric and have a molecular weight of less than about 1500 g/mol. Preferred small molecules are biologically active in that they produce a local or systemic effect in animals, preferably mammals, more preferably humans. In certain preferred embodiments, the small molecule is a drug. Preferably, though not necessarily, the drug is one that has already been deemed safe and effective for use by the appropriate governmental agency or body. For example, drugs for human use listed by the FDA under 21 C.F.R. §§330.5, 331 through 361, and 440 through 460; drugs for veterinary use listed by the FDA under 21 C.F.R. §§500 through 589, incorporated herein by reference, are all considered acceptable for use in accordance with the present invention.

BRIEF DESCRIPTION OF THE DRAWING

The invention is described with reference to the several figures of the drawing, in which.

DETAILED DESCRIPTION OF CERTAIN PREFERRED EMBODIMENTS

Figure 1:
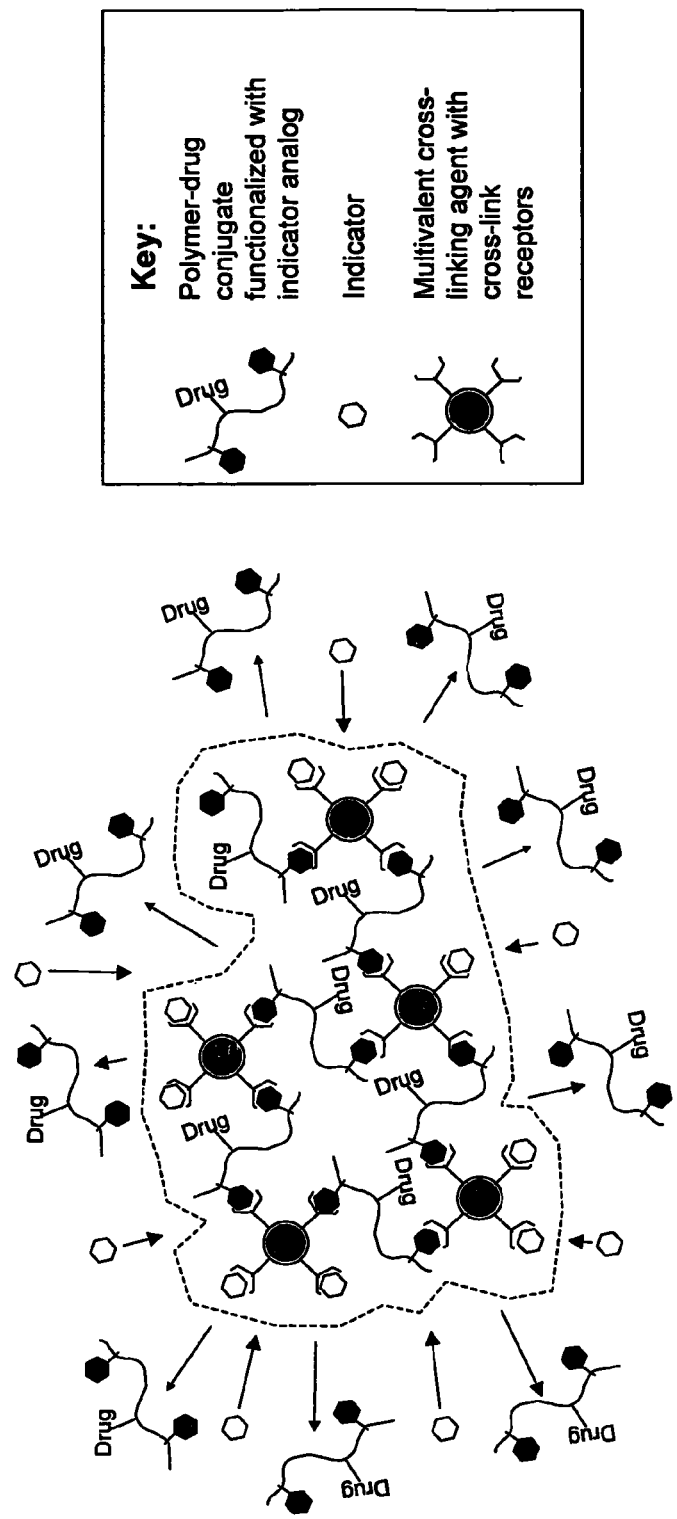
FIG. 1 is a schematic of an exemplary controlled release material comprising an insulin-glycosylated polymer conjugate and a multivalent glucose-binding molecule.

This application refers to a number of published documents including patents, patent applications and articles. Each of these published documents is hereby incorporated by reference.

A. Polymer-Drug Conjugates

In one aspect, the invention provides a conjugate that includes a drug covalently linked to a polymer. The polymer and drug can be directly linked or indirectly linked through a spacer. The spacer may itself be a polymer but can also be a coupling agent, etc. Upon administration, the conjugate is digested by an enzyme that is present at the site of administration thereby releasing a therapeutic agent, e.g., the drug itself or the drug and a portion of the polymer and/or spacer. It is to be understood that the conjugate may be digested by more than one enzyme present at the site of administration. In addition, it will be appreciated that digestion of the conjugate may produce a population of different species, each digested at different points within the spacer and/or polymer and each digested to different extents. These species may be further digested over time after the initial cleavage. This further digestion may occur at the site of administration and/or after they have been absorbed into the systemic circulation. In general, because of the enzymatic degradation, the therapeutic agent is absorbed into circulation more rapidly than the conjugate would be without enzymatic action.

In one set of embodiments, the degradation rate of the conjugate is such that the pharmacokinetic and/or pharmacodynamic behavior of the therapeutic agent are substantially the same as the unconjugated drug. Generally, absorption of the therapeutic agent will lag behind absorption of the unconjugated drug because of the need for enzymatic digestion. In certain embodiments however the lag is minimal. In one embodiment, the similarity in pharmacokinetic and/or pharmacodynamic behavior is observed when the conjugated and unconjugated drugs are administered subcutaneously. For example, from a pharmacokinetic (PK) perspective, the serum concentration curve of the therapeutic agent may be substantially the same as when an equivalent amount of unconjugated drug is administered. Additionally or alternatively, the conjugate may release the therapeutic agent to yield a serum $T_{max}$, a serum $C_{max}$, a mean serum residence time (MRT), a mean serum absorption time (MAT) and/or a serum half-life that is substantially the same as when the unconjugated drug is administered. From a pharmacodynamic (PD) perspective, the conjugate may act on substances within the body in substantially the same way as the unconjugated drug. For example, in the case of an insulin conjugate, the conjugate may affect blood glucose levels in substantially the same way as unconjugated insulin. In this case, substantially similar pharmacodynamic behavior can be observed by comparing the time to reach minimum blood glucose concentration ($T_{nadir}$), the duration over which the blood glucose level remains below a certain percentage of the initial value (e.g., 70% of initial value or $T_{70\% BGL}$), etc. It will be appreciated that these PK and PD characteristics can be determined according to any of a variety of published pharmacokinetic and pharmacodynamic methods (e.g., see Baudys et al., *Bioconjugate Chem.* 9:176-183 (1998) for methods suitable for subcutaneous delivery).

In one embodiment, an inventive conjugate produces pharmacokinetic (PK) parameters such as time to reach maximum serum drug concentration ($T_{max}$), mean drug residence time (MRT), serum half-life, and mean drug absorption time (MAT) that are within 20% of those values determined for the unconjugated drug. More preferably a conjugate produces PK parameters that are within 15% or even 10% of those produce by the unconjugated drug.

For example, in embodiments involving an insulin conjugate for subcutaneous delivery the conjugate may produce an insulin $T_{max}$ between 15-30 minutes, a mean insulin residence time (MRT) of less than 50 minutes, and a mean insulin absorption time (MAT) of less than 40 minutes, all of which are within 20% of those values determined from the human recombinant insulin treatment group. In certain embodiments, the conjugate may produce an insulin $T_{max}$ between 20-25 minutes, a mean insulin residence time (MRT) of less than 45 minutes, and a mean insulin absorption time (MAT) of less than 35 minutes. In certain embodiment, the conjugate may produce a serum half-life of less than 120 minutes, e.g., less than 100 minutes.

In one embodiment, an inventive conjugate produces pharmacodynamic (PD) parameters such as time to reach minimum/maximum blood concentration of a substance ($T_{nadir}$/$T_{max}$) or duration over which the blood level of the substance remains below/above 70%/130% of the initial value ($T_{70\% BL}$/$T_{130\% AL}$).

For example, in embodiments involving an insulin conjugate for subcutaneous delivery the conjugate may produce a glucose $T_{nadir}$ between 45-60 minutes and a glucose $T_{70\%BGL}$ of less than 180 minutes, both of which are within 20% of those determined from the human recombinant insulin treatment group. In certain embodiments the conjugate may produce a glucose $T_{nadir}$ between 50-55 minutes and a glucose $T_{70\%BGL}$ of less than 160 minutes.

In one embodiment, the polymer is susceptible to digestion by the enzyme present at the site of administration. In other embodiments, the spacer is susceptible to digestion by the enzyme. In yet other embodiments, both the polymer and spacer are susceptible to digestion by the enzyme. One skilled in the art will recognize that a number of enzymes are present in the body that could cleave the polymer and/or spacer. Without limitation, these include saccharidases, peptidases, and nucleases. Exemplary saccharidases include, but are not limited to, maltase, sucrase, amylase, glucosidase, glucoamylase, and dextranase. Exemplary peptidases include, but are not limited to, dipeptidyl peptidase-IV, prolyl endopeptidase, prolidase, leucine aminopeptidase, and glicyl glycine dipeptidase. Exemplary nucleases include, but are not limited to, deoxyribonuclease I, ribonuclease A, ribonuclease T1, and nuclease S1.

One skilled in the art will also recognize that, depending on the choice of enzyme, there are a number of polymers and spacers that are susceptible to enzymatic cleavage. For example, in cases where saccharidase degradation is desired, polysaccharide polymers and spacers can be used. For example, Sauer et al. describe the structure/function relationships between the sacchridase glucoamylase with regard to its binding and catalytic behavior (*Biochim Biophys Acta.* 2000 Dec. 29; 1543 (2): 275-293). Thus, without limitation, a conjugate that includes a polysaccharide comprising repeating chains of 1,4-linked alpha-D-glucose residues will be degraded by alpha-amylases. Suitable polysaccharides include glycogen and partially digested glycogen derived from any number of sources, including but not limited to, sweet corn, oyster, liver (human, bovine, rabbit, rat, horse), muscle (rabbit leg, rabbit abdominal, fish, rat), rabbit hair, slipper limpet, baker's yeast, and fungus. Other polysaccharide polymers and spacers that one could use include carboxylated polysaccharides, $-NH_2$ pendant polysaccharides, hydroxylated polysaccharides, alginate, collagen-glycosaminoglycan, collagen, mannan, amylose, amylopectin, cellulose, hyaluronate, chondroitin, dextrin, chitosan, etc. In cases where peptidase cleavage is desired, polypeptide polymers or polypeptide spacers that contain amino acid sequences recognized by the cleaving enzyme can be used. For example, Thoma et al. describe the structural basis for proline-specific exopeptidases such as human dipeptidyl peptidase IV (*Structure* 11: 947-59, 2003). Thus, without limitation, a conjugate that includes a [-Glycine-Proline-] sequence will be degraded by prolidase. In certain embodiments one could use co-polymers of aminated and non-aminated amino acids, co-polymers of hydroxylated and non-hydroxylated amino acids, co-polymers of carboxylated and non-carboxylated amino acids, co-polymers of the above or adducts of the above. In cases where nuclease degradation is desired, polynucleotide polymers and spacers can be used. For example, Beers describes the role of pancreatic ribonuclease in hydrolyzing polyadenylic acid sequences (*J Biol Chem.* 235:2393-8, 1960). Thus, without limitation, a conjugate that includes a polynucleotide containing an oligomer of sequential adenosine residues will be degraded by ribonuclease A.

The drug used will depend on the disease or disorder to be treated. The conjugates are not limited to any particular drug and may include small molecule drugs or biomolecular drugs. As described below and in the Examples, in certain embodiments, the conjugates may be used to treat diabetes mellitus in which case antidiabetic drugs would be used. Biomolecules that are suitable for this purpose include, but are not limited to, therapeutic proteins and peptides, e.g., insulin, growth hormones, glucagon, leptin, glucagon-like peptide 1 (GLP-1) and GLP-1 analogues. For example, in one embodiment, the conjugate may include insulin covalently linked to glycogen. Instead of insulin one could also use insulin analogues, insulin secretagogues (e.g., sulfonylureas or meglinitides) or insulin sensitizers. Sulfonylureas currently known in the art include chlorpropamide, glibenclamide, gliclazide, glimepiride, glipizide, gliquidone, tolazamide and tolbutamide. Meglinitides currently known in the art include nateglinide and repaglinide. Biguanides (e.g., metformin) are antidiabetic agents that decrease glucose levels by reducing hepatic glucose and increasing preipheral uptake of glucose. These and any other drug can be used in a conjugate of the invention.

The present invention encompasses conjugates that are loaded with one or more drugs and to differing levels. In one embodiment, loading levels in the range of 0.5-15% w/w of drug to conjugate are suitable. As described in the Examples, this range has been found to produce insulin-glycogen conjugates with beneficial characteristics. In certain embodiments loading levels within the narrower range of 5-10% are suitable, and in yet other embodiments a range of 6-8% can be used.

It is to be understood that the techniques of the invention may also be exploited to produce conjugates that are more stable and/or soluble in solution than unconjugated drugs. This can be advantageous in a number of applications besides long term storage. For example, the solubility of native insulin in water is limited which is problematic for pumps and devices that require high concentrations of insulin in order to function (e.g., see Wolpert et al. in *BMJ* 324:1253, 2002). In addition, insulin tends to aggregate at higher temperatures. Jens Brange has reviewed the issues of insulin instability under high temperature, agitation, and non-physiological pH in *Galenics of Insulin: The Physico-chemical and Pharmaceutical Aspects of Insulin and Insulin Preparations*. Springer-Verlag, Berlin, 1987. In this context, the inventors have found that conjugation of insulin to a polymer such as glycogen can produce a conjugate that is more soluble and/or less prone to aggregation than native insulin.

B. Methods of Making Conjugates

In another aspect, the invention provides methods for making inventive conjugates. In general, these methods involve producing a covalent link between a drug and a polymer (optionally via a degradable spacer which may or may not be polymeric). It is to be understood that the drug may be linked to the desired polymer through any number of chemical linkages, including but not limited to amide, ester, ether, isourea, and imine bonds. Exemplary methods are discussed in more detail below and in the Examples.

In certain embodiments, the drug can be linked to the polymer via a natural or chemically added pendant group. For example, in one embodiment, polymers with $-COOH$ pendant groups (carboxyl bearing polymers, or "CBP's") and carboxyl-derivatives with increased reactivity (e.g., acid halides, esters, etc.) may be used. Such polymers may naturally include carboxyl groups or may be modified to include them. Exemplary CBPs include but are not limited to carboxylated polysaccharides (CPS) such as carboxymethylated glycogen. Naturally occurring carboxylated polymers include but are not limited to carboxylated poly(amino acids) such as poly-L-glutamate and poly-L-aspartate that contain peptide linkages that are recognized and cleaved by serum peptidases. The carboxylate content may be varied between 1 and 100% mol COOH/mol amino acid residue by copolymerizing carboxylated amino acids (e.g., amino acids with a carboxyl group in addition to the carboxyl group which becomes part of the polymer backbone) with non-carboxylated amino acids (e.g., amino acids whose only carboxyl group becomes part of the polymer backbone).

In another embodiment, polymers having $-NH_2$ pendant groups ($-NH_2$ bearing polymers, or "NBP's") may be used. Such polymers may be naturally occurring or may be chemically modified to include a primary amine. Examples of the latter type of NBP include, but are not limited to, $-NH_2$ pendant polysaccharides (NPS) such as amino-derivatized glycogen. The degree of $-NH_2$ substitution with respect to monomer may vary between 1 and 100% mol. Other suitable NBP's include, but are not limited to, polynucleotides where one or more of the purine bases has been derivatized with an amine group at the 2' location. Naturally occuring aminated polymers include poly(amino acids) such as copolymers poly-L-lysine (PLL) containing peptide linkages that are recognized and cleaved by serum peptidases. The amine content may be varied between 1 and 100% mol $NH_2$/mol amino acid residue by copolymerizing an aminated amino acid (e.g., an amino acid with an amine in addition to the amine group that eventually becomes part of the polymer backbone) with non-aminated amino acids (e.g., an amino acid whose only amine is that which eventually becomes part of the polymer backbone). Proteins that include epsilon-$NH_2$ lysine groups (and which naturally have alpha-$NH_2$ terminal groups) and peptide linkages that are recognized and cleaved by serum peptidases may also be used.

In another embodiment, polymers having —OH pendant groups (—OH bearing polymers, or "OBP's") may be used. Such polymers may be naturally hydroxylated or may be chemically modified using standard organic chemistry techniques to include a hydroxyl group. Naturally occurring OBP's include, but are not limited to, polysaccharides such as glycogen and maltodextrin and all polynucleotides. In addition, poly(amino acids) such as poly(serine), poly(threonine), poly(tyrosine), and poly(4-hydroxyproline) may also be employed as hydroxylated polymers, provided that they contain peptide linkages that are recognized and cleaved by serum peptidases. The hydroxyl content of the poly(amino acids) may be varied between 1 and 100% mol —OH/mol AA residue by co-polymerizing hydroxylated amino acids with non-hydroxylated amino acids. Of course, carboxyl, amino, and hydroxyl pendant groups may be mixed in a single polymer by co-polymerizing the appropriate amino acids in desired ratios.

In another embodiment, polymers having —SH pendant groups (—SH bearing polymers, or "SBP's") may be used. Such polymers may be naturally sulfhydrylated or may be chemically modified using standard organic chemistry techniques to include a sulfhydryl group.

Co-polymers, mixtures, and adducts of the above polymers may also be used in the practice of the invention. Indeed, such combinations may be particularly useful for optimizing the mechanical and chemical properties of the matrix. Both the choice of polymer and the ratio of polymers in a co-polymer may be adjusted to optimize the stiffness of the matrix and the degradation rate of the component polymer.

Exemplary drugs suitable for use in this invention include but are not limited to those containing —COOH, —$NH_2$, —OH, and —SH reactive moieties. Specific examples include therapeutic peptides and proteins bearing alpha-terminal $NH_2$ and/or epsilon-$NH_2$ lysine groups.

—COOH bearing drugs can be conjugated to OBP's using the procedure outlined by Kim et al. *Biomaterials* 24:4843 (2003). Briefly, the OBP is dissolved in DMSO along with the —COOH functionalized drug and reacted by means of N',N'-dicyclohexylcarbodiimide (DCC) and 4-dimethylaminopyridine (DMAP) as catalysts under a dry atmosphere. The resulting product is precipitated in ethanol, then dissolved in water, and filtered to remove insoluble particles, followed by lyophilization to obtain the pure conjugate. —COOH functionalized drugs can be conjugated to NBP's using a carbodiimide (EDAC) coupling procedure. Using this procedure, the —COOH bearing drug is functionalized by reaction with EDAC in a pH 5 buffer followed by the addition of NBP. The resulting product is ultrafiltered and lyophilized to obtain the pure conjugate —$NH_2$ bearing drugs can be conjugated to CBP's to produce a stable amide bond as described by Baudys et al., *Bioconj. Chem.* 9:176-183 (1998). This reaction can be achieved by adding tributylamine (TBA) and isobutylchloroformate to a solution of the CBP and an —$NH_2$ bearing drug in dimethylsulfoxide (DMSO) under anhydrous conditions followed by separation of conjugated and unconjugated drug using HPLC size exclusion chromatography (HPLC-SEC). —$NH_2$ bearing drugs can alternatively be coupled to OBP's through cyanalation using reagents including, but not limited to, cyanogen bromide (CNBr), N-cyanotriethylammonium tetrafluoroborate (CTEA), 1-Cyano-4-(Dimethylamino)-pyridinium tetrafluorborate (CDAP), and p-nitrophenylcyanate (pNPC). CNBr reactions can be carried out at mildly basic pH in aqueous solution followed by ultrafiltration, separation by HPLC-SEC, and lyophilization. CDAP reactions are carried out in a mixture of DMSO and water at mildly basic pH using triethylamine (TEA) as a catalyst followed by ultrafiltration, separation by HPLC-SEC, and lyophilization. $NH_2$ bearing drugs can be conjugated to NBP's through glutaraldehyde coupling in aqueous buffered solutions containing pyridine followed by quenching with glycine, ultrafiltration, and lyophilization.

—OH functionalized therapeutic agents can be conjugated to OBP's according to the divinylsulfone (DVS) procedure. Using this procedure, OBP is added to a pH 11.4 bicarbonate buffer and activated with DVS followed by addition of an —OH functionalized drug after which glycine is added to neutralize and quench the reaction. The resulting polymer is dialyzed exhaustively against deionized water and finally lyophilized to obtain the pure conjugate.

—SH functionalized drugs can be conjugated to NBP's according to a method described by Thoma et al., *J. Am. Chem. Soc.* 121:5919-5929 (1999). This reaction involves suspending the NBP in anhydrous dimethylformamide (DMF) followed by the addition of 2,6-lutidine and acid anhydride and subsequent precipitation and purification of the reactive intermediate. A —SH functionalized drug is then added to a solution of the intermediate in DMF with triethylamine followed by extensive ultrafiltration and lyophylization to obtain the pure polymer-therapeutic agent conjugate.

In general, the amount of drug that is loaded onto the polymer can be controlled by adjusting the molecular weight of the polymer and/or the level of chemical activation (i.e., when pendant groups are added to the polymer). As discussed in the Examples, this can in turn be used to control the pharmacokinetic and pharmacodynamic profile of the therapeutic agent that is released from the conjugate upon administration. In certain embodiments it may prove advantageous to include a step of purifying the polymer prior to activation and reaction with the drug. This will be particularly advantageous when using naturally occuring polymers (e.g., partially digested glycogen from natural sources) since it will allow for the removal of contaminants, e.g., antigenic proteins.

As discussed in the Examples, the present invention has been exemplified using insulin as a conjugated drug. Thus, in one particular embodiment, insulin is coupled to glycogen (an OBP) using a CNBr coupling procedure. Briefly, glycogen is dissolved in deionized water after which solid CNBr is added to the resulting solution and the pH is maintained constant at 10.7 using 3N sodium hydroxide (NaOH) solution. After stirring for 15 minutes, solid CNBr is added again and the pH maintained constant at 10.7 while stirring for 45 minutes. Insulin is then added to the solution and the pH adjusted to 9.15 using solid sodium bicarbonate. The solution is stirred overnight, ultrafiltered exhaustively against deionized, and lyophilized. The resulting powder is then purified from unconjugated insulin by HPLC-SEC using a 1 M acetic acid mobile phase over a Superdex™ 30 HiLoad 16/60 (Amersham Biosciences, Piscataway, N.J.) packed column. The insulin-glycogen fraction is then lyophilized to obtain the conjugate as a pure white powder.

In another embodiment, the weight percentage of insulin loading can be increased by using CDAP conjugation. Briefly, glycogen is dissolved in a 50:50 mixture of deionized water and dimethylsulfoxide (DMSO). 1-cyano-4-dimethylaminopyridinium tetrafluoroborate (CDAP) is then added dropwise to the glycogen solution at 0° C. After stirring for 5 minutes, triethylamine is added and the solution stirred for another 5 minutes. At this time, dilute HCl is added to remove carbamate groups, neutralize triethylamine, and control the resulting ability of the polymer to react with insulin. The mixture is allowed to stir for 15 minutes. The pH is then adjusted to 10.4 followed by the addition of insulin to the solution and final pH adjustment to 9.15. The solution is stirred overnight, ultrafiltered exhaustively against deionized water, and lyophilized. The resulting powder is then purified from unconjugated insulin by HPLC-SEC using a 1 M acetic acid mobile phase over a Superdex™ 30 HiLoad 16/60 (Amersham Biosciences, Piscataway, N.J.) packed column. The insulin-glycogen fraction is then lyophilized to obtain the conjugate as a pure white powder. Removal of the dilute HCl acid treatment step prior to increasing the pH to 10.4 allows for even higher loading of insulin. As discussed in the Examples, the inventors have also found that adding an amount of glycine during the reaction can increase the solubility of the conjugate. For example, when drugs are conjugated to highly branched functionalized polymers, they are presented in some as high density multivalent chemical entities. If in one case the drug has limited solubility in aqueous solution or in another case, has the tendency to self aggregate, such as is the case with insulin, solution instability and insolubility will be enhanced by the conjugate multivalency. The inventors have discovered that covalent addition of ionically charged side chains to the polymer, such as glycine and ethylenediamine, greatly improves the drug-conjugate solubility and stability in solution.

C. Materials for Controllably Releasing a Conjugate

In another aspect, the invention provides a material for controllably releasing an inventive conjugate in response to the local concentration of a molecular indicator. The material includes a plurality of conjugates and a plurality of multivalent cross-linking agents. According to this aspect, the polymeric component of the conjugate includes an analog of the indicator within its covalent structure. The multivalent cross-linking agents include cross-link receptors that interact with the indicator analog and thereby cross-link the conjugates. These non-covalent interactions are competitively disrupted when an amount of the molecular indicator is present thereby causing the material to release the conjugate in a manner that is dependent on the local concentration of indicator.

In one embodiment, the accessibility and thus the enzymatic degradability of the conjugates within the cross-linked material is minimal. However, as the local concentration of indicator increases, the multivalent cross-linking agents bind to free indicator molecules thereby weakening surface cross-links and allowing conjugates to erode away from the surface of the material. Once released from the cross-linked material, the conjugates are degraded by enzymes present at the site of administration thereby releasing a therapeutic agent which can be absorbed into the circulation. This controlled release scheme is illustrated in FIG. 1.

Indicator and Indicator Analog

As noted above, in this aspect of the invention, the polymeric component of the conjugate includes an analog of the indicator within its covalent structure. As used herein, the term "indicator analog" refers to a chemical group that interacts with a cross-link receptor of the multivalent cross-linking agent in a similar manner to the corresponding indicator molecule. One skilled in the art will recognize that the indicator analog may have essentially the same composition as the indicator itself or may be a chemically related species. It will be appreciated that where the affinity of the cross-link receptor for the indicator and the indicator analog are different, the density of cross-links may need to modified so that the desired amount of conjugate is released for a given local concentration of indicator. The indicator analog may be naturally present within the covalent structure of the polymer (e.g., as part of the backbone or as a side group). Alternatively (or additionally) it may be artificially incorporated into the covalent structure post-polymerization (i.e., as a chemical group that is covalently linked to the polymer through its backbone or side groups). For example, when the indicator is glucose the indicator analog can be a derivative of glucose, lactose, maltose, mannose, mannobiose, mannotriose, etc. In one embodiment the indicator is glucose, the polymer is glycogen (which includes glucose moieties as indicator analogs), and the conjugate is released from the material in response to the local concentration of glucose.

Sugars can be conjugated to polymeric —NH$_2$ groups as described in Thoma et al., *J. Am. Chem. Soc.*, 121:5919 (1999). Briefly, NBP (1 mmol based on —NH$_2$ groups) is suspended in a mixture of dimethylformamide (DMF) and 1 ml of 2,6-lutidine under a dry argon atmosphere. At 0° C., a solution of acid anhydride (3.0 mmol) in 1 ml of DMF is added within 15 minutes, and the resulting clear solution stirred for 16 hr at 0° C. The product is precipitated by dropwise addition to 40 ml of a stirred 1:1 mixture of ethanol and ether. The solid is filtered, washed, and dried under vacuum. 10.0 mg (0.050 mmol) of dried solid is dissolved in 2 ml of DMF containing 2 equivalents of thioglucose (varying alpha/beta anomer ratio), obtained from Sigma Aldrich. Triethylamine is then added at 2 equivalents and stirred at room temperature for 16 h. The mixture is then added dropwise to 30 ml of a 1:1 mixture of ethanol and ether. The precipitate is washed with ethanol and dried under vacuum. The crude product may then be dissolved in deionized water and ultrafiltered exhaustively against fresh deionized water, followed by lyophilization to produce dry NBP-glucose polymer. The degree of glycosylation is easily adjusted by varying the equivalents of thioglucose used in the reaction mixture. In this case, the unreacted —NH$_2$ groups are capped with glycerol by adding an excess (3.0 to 5.0 equivalents) of thioglycerol, obtained from Sigma Aldrich.

Sugars such as glucose or mannose can be conjugated to OBPs using a divinylsulfone (DVS) procedure. Briefly, the OBP is added to a pH 11.4 bicarbonate buffer and activated with DVS. D-mannose or D-glucose is then added and allowed to react for ~1 hr at room temperature, after which glycine is added to neutralize and quench the reaction. The resulting polymer is dialyzed exhaustively against deionized water and finally lyophilized to obtain glycosylated-OBP. OBPs may also be modified with sugars using periodate coupling as described in Mislovicová et al., *Bioconjugate Chem.*, 13:136-142 (2002). 100 mg of OBP is dissolved in 1-3.5 ml of a 0.05 M aqueous solution of sodium periodate (NaIO$_4$) and stirred in the dark at 4° C. for one hour. The volume of periodate solution is varied depending on the degree of hydroxylation of the OBP and the desired extent of reaction. The reaction is stopped by adding 1 ml of ethylene glycol and stirring for one hour. The resulting mixture is dialyzed against water and lyophilized. The resulting dry dialdehyde form of OBP is dissolved in 4 ml of a 0.05 M phosphate buffer, pH 7 at 10 mg/ml. To this solution, 4 ml of a solution of GA or MA in 0.05 M phosphate buffer, pH 7 at 10-50 mg/ml is added along with 2.5 ml of a 10 mg/ml sodium cyanoborohydride (NaCNBH$_3$) solution and the resulting mixture stirred at room temperature for 24 hours. The reaction is then stopped by adding a sodium borohydride (NaBH$_4$) solution in 0.05 M pH 9.5 borate buffer at a concentration of 5 mg/ml to reduce the remaining aldehyde groups. The resulting mixture is stirred for 6 hours at room temperature, after which the pH is adjusted to 7 using 4 M hydrochloric acid (HCl). The resulting solution is ultrafiltered exhaustively against deionized water and lyophilized to obtain pure glycosylated-OBP. In this embodiment, equal volumes of the two reactant (polymer and sugar) solutions are employed to prevent the components from reacting too quickly. The degree of conjugation is controlled by adjusting the concentrations of the solutions.

Multivalent Cross-Linking Agent

Conjugates are cross-linked within the material through interactions between the indicator analogs of the polymers and the cross-link receptors of multivalent cross-linking agents. These interactions are non-covalent and thus reversible. As the local concentration of the indicator increases, it competes with the indicator analog for interactions with the cross-link receptor eventually causing the conjugates to become detached from the multivalent cross-linking agent.

In general, the multivalent cross-linking agent will be selected based on its binding properties for the indicator and its analog. For example, if the indicator is a peptidic hormone then the multivalent cross-linking agent might be prepared by chemically linking two or more copies of a receptor protein or antibody for the hormone. Similarly, if the indicator is a saccharide then the multivalent cross-linking agent might be a multivalent saccharide binding protein. Exemplary multivalent saccharide binding proteins include plant lectins, or phytohemoagglutinins (PHA's), such as concanavalin A (Con A) and those derived from *pisum sativum* (pea), *lathyrus odoratus* (sweet pea), *lens culinaris* (lentil), *narcissus pseudonarcissus* (daffodil), *vicia faba* (fava bean), and *vicia sativa* (garden vetch) as well as human analogues of plant lectins such as human mannan binding protein (MBP, also called mannan binding lectin, Sheriff et al., *Structural Biology*, 1:789-794 (1994); Dumestre-Perard et al., *Molecular Immunology*, 39:465-473 (2002)), human pulmonary surfactant protein A (SP-A, Allen, et al., *Infection and Immunity*, 67:4563-4569 (1999)), human pulmonary surfactant protein D (SP-D, Persson et al., *The Journal of Biological Chemistry*, 265:5755-5760 (1990)), CL-43 (a human serum protein), and conglutinin. One skilled in the art will recognize that any multivalent binding protein may be exploited for use with the invention.

As suggested above, other multivalent cross-linking agents may be constructed by chemically linking multiple monovalent binding proteins, for example, antibodies, cell membrane receptors, lectins, collectins, etc. Still other multivalent molecules may be constructed by chemically linking specific binding fragments of proteins, for example, antibodies, cell membrane receptors, lectins, collectins, etc. Exemplary protein fragments include truncated MBP (Eda et al., *Biosci. Biotechnol. Biochem.*, 62:1326-1331 (1998)), truncated conglutinin (Eda et al., *Biochem. J.* 316:43 (1996)), truncated SP-D (Eda et al., *Biochem. J.* 323:393 (1997)), and the glucose/galactose binding protein of *E. Coli* (Salins et al., *Analytical Biochemistry* 294:19-26 (2001)). In addition, a variety of monovalent ligand-binding proteins are available commercially from Sigma-Aldrich, including folate-binding protein, thyroxine-binding globulin, and lactoferrin.

Monovalent molecules and fragments may be linked directly to one another or to polymer scaffolds. Suitable scaffold materials include but are not limited to the CBPs, NBPs, and OBPs described above. In certain embodiments, proteins may be attached to these polymers to form multivalent cross-linking agents using the insulin-conjugation procedures that are described in the Examples or other standard organic chemistry reactions (see March, "Advanced Organic Chemistry", 5th ed. John Wiley and Sons, New York, N.Y., 2001).

In certain embodiments, mono- or multivalent binding proteins can be synthesized by rational computational design followed by site directed mutagenesis of ligand-binding proteins as described in Looger et al., *Nature* 423:185-190 (2003). For example, in one embodiment a soluble L-Lactate binding protein can be synthesized by introducing random modification to wild-type glucose binding protein (GBP), ribose binding protein (RBP), arabinose-binding protein (ABP), glutamine binding protein (QBP), and/or histidine binding protein (HBP). The monovalent L-lactate binding protein is made multivalent by attaching several protein molecules to a polymer. A conjugate with a polymer comprising lactate moieties can be produced based on the procedure of de Jong (de Jong et al., *Journal of Controlled Release* 71:261-275 (2001)). The lactate functionalized polymer can then be cross-linked with the multivalent lactate-binding protein to produce a lactate-responsive delivery system. Elevated L-lactate concentrations are indicative of several medical conditions including extreme muscle fatigue.

It is to be understood that any of these multivalent cross-linking agents may be chemically modified with short-chain polymers, e.g., polyethyleneglycol (PEG), to reduce in vivo immunogenic responses (e.g., reduced mitogenicity and/or antigenicity). For example, the terminal-NH$_2$ and epsilon-amino lysine groups of protein-based cross-linking agents can be reacted with activated PEG molecules (e.g., without limitation N-hydroxysuccinimide activated PEG, succinimidyl ester of PEG propionic acid, succinimidyl ester of PEG butanoic acid, succinimidyl ester of PEG alpha-methylbutanoate), in aqueous solution at room temperature followed by ultrafiltration to remove unreacted PEG and lyophilization to obtain the pure pegylated crosslinking agent. Other exemplary monovalent chemical compounds that can be used to modify a multivalent cross-linking agent include natural and synthetic amino acids, other water soluble but non-PEG-containing polymers such as poly(vinyl alcohol), reagents that can be easily coupled to lysines, e.g., through the use of carbodiimide reagents, and perfluorinated compounds.

In one embodiment, the cross-linked material becomes an insoluble hydrogel. The hydrogel degrades as free indicator molecules compete for the interactions between the cross-linking agent and the indicator analog. The hydrogel degrades in a layer-by-layer fashion from the outside in, allowing the conjugate to be released at an approximately constant rate as the hydrogel degrades. The hydrogel may be injected into a patient. In one embodiment, injection is done subcutaneously. Even where a patient requires long term treatment, the degradation mechanism of the material can reduce the frequency of injections by preventing the therapeutic agent from being wasted. The agent is only released as needed, not constantly. As described in U.S. Patent Application Publication No. 2004-0202719, the cross-linked material may also be in the form of particles. These can be prepared in aqueous solution through self assembly by mixing dilute solutions of the conjugate and multivalent cross-linking agent.

In one embodiment, the conjugate includes insulin (drug) covalently linked to glycogen (polymer) and the multivalent cross-linking agent is a multivalent glucose-binding molecule (multi-GBM). The glycogen naturally contains glucose moieties within the backbone and on side groups that serve as the indicator analogs for the multi-GBM. In certain embodiments, Con A or pegylated Con A may be used as the multi-GBM, and when combined with the insulin-glycogen conjugate will form an insoluble hydrogel. While incorporated within the cross-linked hydrogel, the insulin-glycogen amylase degradation occurs at a fraction of the rate of uncrosslinked insulin-glycogen. However, as the glucose concentration in the environment of the hydrogel increases, the insulin-glycogen is de-crosslinked and released from the material. The insulin-glycogen released by glucose from the matrix is then degraded by amylases present at the site of administration thereby releasing insulin molecules (optionally with a portion of the glycogen polymer attached) with essentially the same pharmacokinetic and pharmacodynamic behavior as unconjugated insulin.

D. Methods of Using Conjugates and Materials for Controllably Releasing a Conjugate In another aspect, the present invention provides methods of using inventive conjugates and materials for controllably releasing a conjugate. The inventive conjugates and materials can be used in any application. Generally, the conjugates and materials are suitable for delivering drugs. Thus, inventive conjugates can be used alone to deliver a drug or can be used in the context of an inventive material that controllably releases the conjugate in response to an indicator at the site of administration.

When used alone, an inventive conjugate can be administered as a pharmaceutical composition with one or more inactive agents such as a sterile, biocompatible carrier including, but not limited to, sterile water, saline or buffered saline. The invention encompasses treating a disease by administering the pharmaceutical compositions of the invention. Although the pharmaceutical compositions of the present invention can be used for treatment of any subject (e.g., any animal) in need thereof, they are most preferably used in the treatment of humans. The conjugates of this invention can be administered to humans and other animals by a variety of routes including oral, intravenous, intramuscular, intra-arterial, subcutaneous, intraventricular, transdermal, rectal, intravaginal, intraperitoneal, topical (as by powders, ointments, or drops), bucal, or as an oral or nasal spray or aerosol. In general the most appropriate route of administration will depend upon a variety of factors including the nature of the drug (e.g., its stability in the environment of the gastrointestinal tract), the condition of the patient (e.g., whether the patient is able to tolerate oral administration), etc. Subcutaneous injection is a preferred route of administration. General considerations in the formulation and manufacture of pharmaceutical compositions may be found, for example, in *Remington's Pharmaceutical Sciences*, 19th ed., Mack Publishing Co., Easton, Pa., 1995.

When used in the context of an inventive material, the conjugates can be used to deliver a therapeutic agent to a patient in a controlled manner. Thus in one embodiment the present invention provides a method for controllably releasing a conjugate. This method simply involves administering an inventive cross-linked material to a patient in need thereof. In one embodiment, the accessibility and thus the enzymatic degradability of the conjugates within the administered material is minimal. However, as the local concentration of indicator increases, the multivalent cross-linking agents of the material bind to free indicator molecules thereby weakening surface cross-links and allowing conjugates to erode away from the surface of the material. Once released from the cross-linked material, the conjugates are degraded by enzymes present at the site of administration thereby releasing a therapeutic agent which can be absorbed into the circulation.

In certain embodiments, the material is administered subcutaneously, e.g., by injection. The material can be dissolved in a biocompatible carrier for ease of delivery. For example, the biocompatible carrier can be an aqueous solution including, but not limited to, sterile water, saline or buffered saline.

According to the methods of treatment of the present invention, the disease of interest is treated in a patient such as a human or other mammal by administering to the patient a therapeutically effective amount of a drug in the form of a conjugate, in such amounts and for such time as is necessary to achieve the desired result. In one embodiment, the material includes an insulin-glycogen conjugate and the material is used to treat diabetes mellitus. By a "therapeutically effective amount" of a drug is meant a sufficient amount of the drug to treat (e.g., to ameliorate the symptoms of, delay progression of, prevent recurrence of, delay onset of, etc.) the disease at a reasonable benefit/risk ratio, which involves a balancing of the efficacy and toxicity of the therapeutic agent. In general, therapeutic efficacy and toxicity may be determined by standard pharmacological procedures in cell cultures or with experimental animals, e.g., by calculating the $ED_{50}$ (the dose that is therapeutically effective in 50% of the treated subjects) and the $LD_{50}$ (the dose that is lethal to 50% of treated subjects). The $ED_{50}/LD_{50}$ represents the therapeutic index of the agent. Although in general therapeutic agents having a large therapeutic index are preferred, as is well known in the art, a smaller therapeutic index may be acceptable in the case of a serious disease, particularly in the absence of alternative therapeutic options. Ultimate selection of an appropriate range of doses for administration to humans is determined in the course of clinical trials.

It will be understood that the total daily usage of an inventive conjugate for any given patient will be decided by the attending physician within the scope of sound medical judgment. The specific therapeutically effective dose level for any particular patient will depend upon a variety of factors including the disorder being treated and the severity of the disorder; the activity of the specific drug employed; the specific composition employed; the age, body weight, general health, sex and diet of the patient; the time of administration, route of administration and rate of excretion of the specific drug employed; the duration of the treatment; drugs used in combination or coincidental with the specific drug employed; and like factors well known in the medical arts.

E. Kits

In another aspect the present invention provides kits that include an inventive conjugate and other reagents for preparing a material that controllably releases a conjugate in response to the local concentration of an indicator. The kit includes separate containers that include a plurality of conjugates and a plurality of multivalent cross-linking agents. The polymeric component of the conjugate includes an analog of the indicator within its covalent structure. The multivalent cross-linking agents include cross-link receptors that can interact with the indicator analog and thereby cross-link the conjugates. When the conjugates and multivalent cross-linking agents of the kit are mixed a cross-linked material is formed. The non-covalent interactions between the indicator analogs of the conjugate and the cross-link receptors of the multivalent cross-linking agents are competitively disrupted when an amount of the molecular indicator is present thereby causing the material to release the conjugate in a manner that is dependent on the local concentration of indicator. In one embodiment, the material is designed for subcutaneous delivery and the kit includes a syringe. The kit may also include instructions for mixing the conjugates and multivalent cross-linking agents to produce the cross-linked material.

EXAMPLES

I. Methods of Making Exemplary Conjugates

This first set of examples describes various methods for making exemplary conjugates. The examples also include assays for purifying and assaying the starting ingredients and final products. It is to be understood that these methods can be modified to produce other conjugates that fall within the scope of the invention.

Example 1

Insulin and Glycogen

Insulin

Human recombinant insulin (HRI) is a well established and well characterized biologic protein made from *E. coli*. HRI is readily available in large, pharmaceutical-grade quantities from a number of manufacturers, including Eli Lilly, Novo Nordisk, and Diosynth. Insulin activity can be determined using an in vitro insulin receptor binding assay (e.g., see Example 13) and in vivo pharmacokinetic and pharmacodynamic studies using SD rat models (e.g., see later Examples).

Glycogen

Glycogen can be produced from Golden Bantam sweet corn (Curry Seed Company, Elk Point, S.D.) according to a modified procedure (Morris and Morris, *J. Biol. Chem.* 130: 535-544, 1939). Briefly, 10 g of moist sweet corn kernels are ground and extracted with 3×100 ml of deionized water. The combined extracts are strained to remove coarse particles, and filtered through a fritted funnel to remove insoluble starches. The extract is then concentrated to one third the volume by boiling, and the hot solution is then filtered by vacuum filtration to remove insolubles. The ~100 ml of extract is allowed to cool to room temperature, and 300 ml of glacial acetic acid is added, which causes glycogen to precipitate out of solution. The glycogen precipitate is recovered by centrifugation at 5,000×g (Allegra 21R, Beckman Coulter, Fullerton, Calif.). The recovered glycogen is dissolved in 10M potassium hydroxide, and the resulting solution is boiled for 1 hour to destroy soluble protein. The solution is cooled, and the glycogen is precipitated with an excess of ethanol and recovered by centrifugation at 5,000×g. The glycogen precipitate is redissolved in potassium hydroxide and the process repeated once more to eliminate any remaining protein in the sample. The final glycogen precipitate is then lyophilized (Freezemobile, Virtis, Gardiner, N.Y.) to remove water and ethanol, and the synthesis provides 1.2 g (12% of initial weight of corn) of purified, protein-free corn glycogen as a dry powder. The final product can be characterized by nuclear magnetic resonance (NMR) for purity, carbon, hydrogen, and nitrogen (CHN) analysis for residual protein content and purity, and size exclusion chromatography for molecular weight distribution analysis. If further purification is desired, the lyophilized corn glycogen product can be made free of impurities according to the method of Example 4. The highly purified glycogen fractions are lyophilized and then used subsequently in the synthesis of inventive conjugates.

Example 2

Generalized CNBr Conjugation Method

This example describes a generalized method for making insulin-glycogen conjugates using cyanogen bromide (CNBr) as a coupling agent. Briefly, a known mass of glycogen is dissolved in deionized water at a concentration of 10 mg/ml. Solid CNBr is added to the resulting solution at a CNBr to glycogen mass ratio between 0.05 and 1.5 and the pH maintained constant at 10.7+/−0.2 using 3N sodium hydroxide (NaOH) solution. After stirring for 15 minutes, another equal mass of solid CNBr equal is added and the pH maintained constant at 10.7+/−0.2 while stirring for 45 minutes. Insulin is then added to the solution at an insulin to glycogen mass ratio between 0.05 and 0.60 and the pH adjusted to 9.15 using solid sodium bicarbonate. The solution is stirred overnight, ultrafiltered exhaustively against deionized water using a 50 kDa MWCO polyethersulfone disc membrane filter (Millipore, Bedford, Mass.), and lyophilized. The resulting powder is then purified from unconjugated insulin by gel filtration HPLC (Waters, Milford, Mass.) using a 1 M acetic acid mobile phase over a Superdex™ 30 HiLoad 16/60 (Amersham Biosciences, Piscataway, N.J.) packed column. The insulin-glycogen fraction is then lyophilized to obtain the conjugate as a pure white powder.

Example 3

Generalized CDAP Conjugation Method

This example describes a generalized method for making insulin-glycogen conjugates using cyanodimethylamino-pyridinium tetrafluoroborate (CDAP) as a coupling agent. This synthesis was used to prepare various insulin-glycogen conjugates that are described in later Examples. The inventors have found that this method produces increased insulin loading as compared to the CNBr method of Example 2. Briefly, 8.0 g of glycogen is dissolved in 160 ml of 25 mM HEPES, 0.15 M NaCl, pH 9.0. 2.4-12.0 mL of a 1.0M CDAP solution in DMSO is added dropwise to the glycogen solution at 0° C. After stirring for 1 minute, a volume equal to that of the CDAP solution consisting of 0.2M triethylamine (TEA) is added dropwise over one minute. At this time, the pH of the reaction solution is adjusted to 9.0 using 1.2N HCl. Then, 80-2000 ml of a 10 mg/ml insulin solution in a 20 mM HEPES (pH 9.0) solution is added over the next three minutes and the pH adjusted again to 9.0 using 0.3N NaOH. Finally, in some cases 1.6 ml of a 100 mg/ml glycine solution in 100 mM HEPES buffer containing 0.15M NaCl (pH 9.0) can be added. In other cases, amine-functionalized sugars such as mannosamine, glucosamine, and other glucose or mannose-containing sugars. The inventors have found that the addition of the glycine step increases the solubility of the conjugate. The entire reaction mixture is slowly stirred at room temperature overnight.

The resulting mixture is then diluted by a factor of two with 1 M acetic acid and purified from unconjugated insulin, low MW reaction byproducts, and reagents by gel filtration HPLC (Waters, Milford, Mass.) using a 1 M acetic acid mobile phase over a Superdex™ 30 HiLoad 16/60 (Amersham Biosciences, Piscataway, N.J.) packed column. In some cases, it is necessary to repeat this procedure one or to more times to ensure complete removal of unconjugated insulin. The final mixture is then purified from acetic acid by gel filtration HPLC (Waters, Milford, Mass.) using a pH 8.0, 20 mM HEPES buffer containing 0.150 M NaCl mobile phase over a Superdex™ 30 HiLoad 16/60 (Amersham Biosciences, Piscataway, N.J.) packed column. Finally, the collected fraction is precipitated by adding two volumes of a 50:50 (v/v) mixture of ethanol and ether, washed, and dried under vacuum at room temperature overnight.

Example 4

Insulin Conjugated to Glycogens from Different Sources

Insulin-glycogen conjugates can be prepared using glycogen or partially digested glycogen derived from any number of sources, including but not limited to, sweet corn, oyster, liver (human, bovine, rabbit, rat, horse), muscle (rabbit leg, rabbit abdominal, fish, rat), rabbit hair, slipper limpet, baker's yeast, and fungus. For example, these glycogens can be covalently linked to insulin using the CNBr or CDAP methods of Examples 2 and 3.

Commercial glycogen preparations generally contain protein contaminants. In certain embodiments it is advantageous to remove these contaminants before the drug is loaded onto the glycogen. The resulting conjugate preparations are purer and have a higher drug load per gram of glycogen. This example describes a generalized method for producing protein-free glycogen. The purification procedure involves heating the glycogen in concentrated alkali. This takes advantage of the fact that macromolecules other than polysaccharides (particularly proteins) are destroyed by alkali. In addition, oxygen has minimal solubility in hot alkali, so random oxidative damage to the glycogen is minimized. First, 30 g of glycogen is dissolved in 200 ml of 30% potassium hydroxide and heated in a covered Erlenmeyer flask in a boiling water bath for 2 hours. Any sediment that is produced after cooling is removed by centrifugation. Thereafter, the glycogen solution is transferred to a 1 L beaker and three volumes of ethanol are slowly stirred in. The resulting precipitate is centrifuged and washed twice with a 75% ethanol solution in water. It is then redissolved in 200 ml of water and the precipitation process repeated until the alkali is removed. The final traces of alkali are removed by neutralizing the glycogen solution with acetic acid before the final precipitation. Thereafter, the glycogen is washed twice with pure ethanol and then twice with ether and allowed to dry to produce protein-free glycogen. The inventors have found that insulin loading is increased when purified glycogen is used instead of commercial unpurified glycogen.

Example 5

Conjugation of Glycogen with Non-Human Insulin, Insulin Analogues, Etc.

Instead of human insulin-glycogen conjugates one can prepare glycogen conjugates that include non-human insulin or insulin analogues (i.e., peptides with insulin like bioactivity that differ from insulin by one or more substitutions, additions or deletions). For example, these conjugates can be prepared using the CNBr or CDAP methods of Examples 2 and 3.

Example 6

Symlin-Glycogen Conjugate

The peptidic anti-diabetic drug symlin (pramlintide acetate) is derived from the natural peptide amylin. It can also be conjugated with glycogen (and other OBPs), e.g., using the CNBr or CDAP methods of Examples 2 and 3.

Example 7

Secretagogue-Glycogen Conjugates

Peptidic insulin secretagogues (e.g., GLP-1 or the GLP-1 analogue exanitide) can be coupled to glycogen (and other OBPs) by the CNBr method used to conjugate insulin and glycogen (see Example 2). These peptidic secretagogues can also be conjugated with glycogen using the CDAP coupling method of Example 3.

Sulfonylureas (SU), such as glibenclamide, can be conjugated to glycogen (and other OBPs) according to the procedure outlined in Kim et al. *Biomaterials* 24:4843 (2003). Briefly, the OBP is dissolved in dimethylsulfoxide (DMSO) with the sulfonylurea and reacted by means of N',N'-dicyclohexylcarbodiimide (DCC) and 4-dimethylaminopyridine (DMAP) as catalysts. The reaction is carried out for 48 hours under argon and the dicyclohexylurea removed by filtration. The product is precipitated in ethanol, then dissolved in water, and filtered to remove insoluble particles. Following lyophilization, the product is further purified by dialysis, and lyophilized to obtain a pure OBP-SU product. An SU-conjugated pullulan obtained by this procedure was shown to possess dose-dependent insulinotropic action (see Kim et al. *Biomaterials* 24:4843 (2003)).

Example 8 rHGH-Glycogen Conjugates

The peptidic drug symlin recombinant human growth hormone (rHGH) can also be conjugated with glycogen (and other OBPs), e.g., using the CNBr or CDAP methods of Examples 2 and 3.

Example 9

Glucagon-Glycogen Conjugates

The peptidic drug glucagon can also be conjugated with glycogen (and other OBPs), e.g., using the CNBr or CDAP methods of Examples 2 and 3.

Example 10

Degree of Conjugation by Amino Acid Analysis

This example describes a generalized method for determining the degree of conjugation of a peptidic drug (e.g., insulin) by amino acid analysis (UCLA Biopolymers Laboratory, Los Angeles, Calif.). This method was used to characterize some of the conjugates that are described in later Examples. Purified conjugate is dissolved at 2.5 mg per mL in 1×PBS buffer free from calcium and zinc ions. The samples are dried, hydrolyzed with 6N hydrochloric acid, and the contents analyzed by an amino acid analyzer (e.g., Beckman 6300 model, Beckman-Coulter, Fullerton, Calif.). The peptidic content is calculated based on the relative concentrations of detected amino acids, and the samples are run in duplicate to ensure an accurate reading.

Example 11

Degree of Purity by SDS-PAGE

This example describes a generalized method for determining the amount of unconjugated peptidic drug (e.g., insulin) in a sample of conjugate using SDS-PAGE. This method was used to characterize some of the conjugates that are described in later Examples. First, Laemmli sample buffer is made by mixing the sample with 950 µl of 1×Laemmli Sample Buffer (Bio-Rad, Hercules, Calif.). No mercaptoethanol is used in this particular assay. The desired sample is diluted in 1×PBS buffer to a concentration between 0.5 and 5 mg/ml. 25 µl of this solution is pipetted into a microcentrifuge tube, followed by 50 µl of 1×Laemmli Sample Buffer solution. The centrifuge tube is closed, vortexed briefly, and then placed into boiling water for 5 min. After boiling, the sample is cooled in ice-cold water. The desired samples are pipetted into a BioRad 15-well (15 µl A capacity) precast 15% polyacrylamide gel and run at 150V for 70 minutes. The desired samples are run against a mixture of proteins that act as molecular weight standards. After running the gel, the protein bands are fixed in the gel using a 40:10:50 methanol:acetic acid:water mixture by volume for 15 minutes, followed by washing twice with water. The bands are revealed by staining with colloidal Coomassie blue stain for 1.5 hours. The background staining is removed from the gel by 3× washing in DI water. The drug-polymer conjugate, due to its high molecular weight remains near the top of the gel, while "free" drug and other protein impurity bands, if present, migrate to the bottom of the gel. Pictures of the bands are taken by placing the developed gels on a light table and capturing images of the gel with a digital camera attached to a personal computer. If necessary, the relative densities of electrophoretic bands are quantitatively measured by AlphaImage software.

Example 12

Degree of Purity by Analytical SEC-HPLC

This example describes the use of gel filtration chromatography (GFC) to determine the amounts of unconjugated drug remaining in a sample of conjugate after purification. This method was used to characterize some of the conjugates that are described in later Examples. Briefly, a 10-50 mg/ml solution of the conjugate dissolved in aqueous buffer is injected into an HPLC (Waters Corporation, Milford, Mass.) equipped with a Sephacryl HiPrep 16/60 column (Amersham Biosciences, Piscataway, N.J.) equilibrated at room temperature with a 5-20% acetic acid mobile phase and a UV absorbance detector operating at 280 nm. The column is eluted with the same buffer at a flow rate of 1.0 ml/min. When used to assay an insulin-glycogen conjugate, the conjugated insulin generally elutes between 40 and 90 min under these conditions, whereas unconjugated insulin elutes between 90 and 180 min. The relative amount of conjugated versus unconjugated drug is determined by the ratio of the unconjugated peak area to the total peak area (unconjugated+conjugated). The absolute amount of unconjugated drug in the sample is determined by comparing the peak area to a peak area calibration curve obtained for a set of known drug standards. The mass of unconjugated drug divided by the total mass of injected conjugate yields the mass % of unconjugated drug per conjugate.

II. In vitro Assays of Exemplary Conjugates

This second set of examples describes various experiments investigating the in vitro properties of some exemplary conjugates.

Example 13

Generalized Assay for Insulin-Polymer Conjugate Bioactivity In vitro

This example describes a generalized method for assaying the bioactivity of insulin-polymer conjugates using Hep G-2 cells that express a human insulin receptor. This method was used to characterize some of the insulin containing conjugates that are described in later Examples. The in vitro assay can be used to measure the insulin activity and pharmacologic action of a particular insulin-polymer conjugate. Hep G-2 (hepatocytes) are seeded in 24-well plates at a density of 4×105 cells/well, fed three days after subculture, and used within 3 days for experimentation.

Cell culture media is removed from the wells, and the cells are rinsed with calcium and magnesium free phosphate-buffered saline. 450 uL of binding buffer (118 mM sodium chloride, 5 mM potassium chloride, 1.2 mM magnesium sulfate, 8.8 mM dextrose), 1 mg/mL bovine serum albumin, and 100 mM Hepes buffer at pH 8, and 50 uL of unlabeled conjugate at various concentrations 0.1-1000 ug/mL in binding buffer (1.9% wt. insulin) are added per well. Next, 50 uL of a 2 ug/mL $^{125}$I-labeled recombinant human insulin (1-2×10$^4$ cpm, Amersham Biosciences, Piscataway, N.J.) is added to each well. The plates are then incubated at 15° C. for 6 hours. The buffer is aspirated, and the cells are washed 3× with ice-cold sodium chloride solution, and the contents of each well are solubilized with 0.1% sodium dodecyl sulfate solution. The plates are shaken gently to detach the cells and the contents of each well are transferred into counting tubes. Radioactivity is determined using a gamma counter (20/20 series, Isodata, Inc., Rolling Meadows, Ill.). The radioactivity in solution allows for a determination of the ratio of bound to free $^{125}$I-insulin versus the concentration of unlabeled insulin-polymer conjugate, a measure of the relative bioactivity.

The assay can be repeated with insulin-polymer conjugates that have been subjected to enzymatic digestion. For example, when analyzing an insulin-glycogen conjugate one group can be preincubated at 37° C. with a 10 U/mL solution of a-amylase (porcine, Sigma Aldrich, St. Louis, Mo.), while another group is preincubated at 37° C. with rat serum (Sigma Aldrich, St. Louis, Mo.) so that the insulin-glycogen conjugate is digested in the presence of α-amylase and serum amylases prior to addition to the wells containing Hep G-2 cells.

Example 14

Insulin-Glycogen Conjugate Digestion In vitro

This example demonstrates insulin-glycogen degradation in the presence of amylases. As previously discussed, once an insulin-glycogen conjugate is released from an inventive glucose-responsive material, it is digested by amylases that breakdown the large molecular weight insulin-glycogen conjugate into low molecular weight conjugates in vivo. As shown in other Examples, these conjugates have been found to absorb, act, and eliminate in substantially the same manner as human recombinant insulin. An in vitro amylase digestion assay was performed to qualify the proposed insulin-glycogen degradation mechanism. Briefly, insulin-glycogen synthesized according to the CDAP coupling method of Example 3 using Type IX glycogen from bovine liver (Sigma Aldrich, St. Louis, Mo.) was incubated with a number of different human saliva concentrations to demonstrate how it degrades into free insulin in the presence of amylase. The saliva sample was serially diluted 1:2 in 1×PBS buffer to 1:512.90 µL aliquots of each of the 1:4, 1:16, 1:64, 1:128, 1:256, and 1:512 dilutions were added to pre-prepared microcentrifuge tubes containing 90 µL of undiluted insulin-glycogen. These samples as well as a sample containing 90 µL of 1×PBS and 90 µL of undiluted conjugate were vortexed and then placed in an incubator/shaker set at 37° C. for 15 min. After incubation, 25 µL of each sample was added to 50 µL of Lamelli buffer and the combination was vortexed prior to being loaded on a 4-15% Tris-HCl SDS PAGE gel. In addition to the incubated samples, a molecular weight ladder and high and low insulin standards were also run (with the high insulin standard at 2.5 mg/mL and the low insulin standard at 0.25 mg/mL). The gels were run in SDS running buffer for 45 minutes to an hour at a constant voltage of 150 V. Under these conditions, the amylase completely digested the insulin-glycogen conjugate into native MW insulin at the 1:16 dilution level as quantified by the relative band density of high MW conjugate to that of native MW insulin.

III. In vivo Assays of Exemplary Conjugates

This third set of examples describes various experiments investigating the in vivo properties of some exemplary conjugates.

Example 15

Generalized Assay for Insulin-Polymer Conjugate Bioactivity In vivo

This example describes a generalized method for assaying the bioactivity of insulin-polymer conjugates using an enzyme-linked immunosorbent assay (ELISA). This method was used to characterize some of the insulin containing conjugates that are described in later Examples.

Subcutaneous injections of insulin-polymer conjugates or insulin controls are administered at a dose between 1 and 10 equivalent U insulin/kg body weight behind the neck of fasted normal diabetic rats (Male Sprague-Dawley, 200-250 g, n=2-4). Blood samples are collected via tail vein bleeding at −15 and 0 minutes, and at 15, 30, 45, 60, 90, 120, 180, 240, 300 and 360 minutes after injection. Blood glucose values are measured using commercially available test strips (Precision Xtra, Abbott Laboratories, Abbott Park, Ill.). The remaining blood is centrifuged to obtain serum and stored in a freezer until measured for serum insulin levels. Serum insulin is measured using an ELISA kit (ALPCO Diagnostics, Windham, N.H.). Pharmacodynamic (PD) parameters such as time to reach minimum blood glucose concentration ($T_{nadir}$) and duration over which the blood glucose level remains below 70% of initial value ($T_{70\% \, BGL}$), are determined according to published methods for subcutaneous delivery. Pharmacokinetic (PK) parameters such as time to reach maximum serum insulin concentration ($T_{max}$), mean insulin residence time (MRT), and mean insulin absorption time (MAT), are determined according to published methods for subcutaneous delivery using commercially available ELISA assays (ALPCO Diagnostics, Windham, N.H.). The blood glucose depression curve and corresponding serum insulin profile for each formulation may then be compared to those obtained for an insulin control to determine any differences in the timing and extent of the insulin action.

Example 16

In vivo Bioactivity of Insulin-Glycogen Conjugate vs. Insulin

This example compares the in vivo bioactivity of an insulin-glycogen conjugate with that of unmodified recombinant human insulin (RHI). The insulin-glycogen conjugate was synthesized according to the general method described in Example 2 using 1 g of commercially available, unpurified oyster glycogen (Type II, Sigma-Aldrich, St. Louis, Mo.), a CNBr to glycogen mass ratio of 0.68, and a human recombinant insulin (Sigma-Aldrich, St. Louis, Mo.) to glycogen mass ratio of 0.60. The resulting purified material contained 1.0 wt % of insulin per insulin-glycogen conjugate as measured using the method described in Example 10. The bioactivity of the insulin-glycogen conjugate was evaluated at 2.5 equivalent U of insulin/kg according to the general method described in Example 13. In addition, the bioactivity of unmodified human recombinant insulin was evaluated at 1 U/kg.

Example 17

In vivo Safety of Insulin-Glycogen Conjugate

Subcutaneous injections of (i) tris buffer, pH 7.4 with 150 mM sodium chloride (negative control), (ii) insulin-glycogen conjugate in tris buffer, (iii) human recombinant insulin in tris buffer, and (iv) human recombinant insulin plus complete Freund's adjuvant (positive control), were each administered using a 0.25 ml injection behind the neck of two separate fasted normal rat groups (Sprague Dawley, male, 200-225 g, n=4) on days 0, 7, 14, 21, and 28. The insulin-glycogen conjugates were prepared according to the method of Example 3. As rats gained weight over the course of the study, the volume of injection was adjusted to keep the dose per kilogram of body weight constant. On days 7-28, positive control groups received mixtures of recombinant human insulin plus incomplete Freund's adjuvant.

Figure 2:
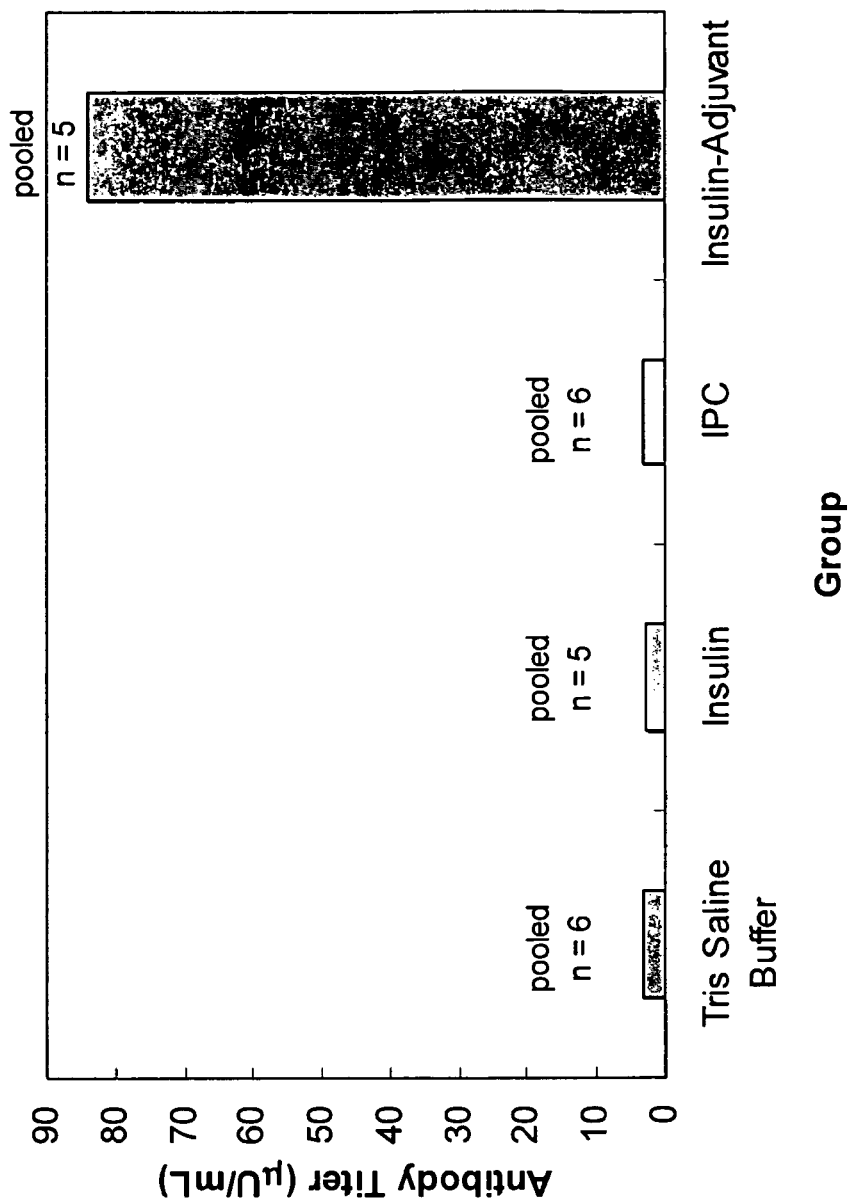
FIG. 2 shows serum total Ig-class anti-insulin antibody titers obtained for male SD rats after week 8 of an immunization protocol using saline, insulin, insulin-glycogen conjugate, and insulin plus adjuvant solutions. Titers are expressed as μU of insulin bound per ml of serum assayed. Solutions were injected s.c. into male Sprague-Dawley (SD) rats weighing 200-250 g (n=5 or 6) each week for four weeks. Blood was collected each week for up to eight weeks and pooled to quantify the titer of all Ig-class anti-insulin antibodies using a radioimmunoassay (RIA) technique (Esoterix, Inc., Calabasas Hills, Calif.).

Serum samples were collected via tail vein bleeding on days 28 and 56, and serum concentrations of specific anti-human insulin antibodies of all Ig classes were measured using a Total Insulin Antibody (Total IAB) assay (Esoterix, Calabasa Hills, Calif.). Briefly, test and control serum samples were first treated with acidified-charcoal to remove unbound insulin and strip the insulin from IAB complexes. The insulin-bound charcoal was removed from the serum by centrifugation. The IAB-containing supernatant was then incubated for 72 hours at 4° C. with radiolabeled insulin. As a control for nonspecific binding (NSB), unlabeled insulin was added to replicate samples to compete with radiolabeled insulin for IAB binding. Polyethylene glycol (PEG) was added to precipitate antigen-antibody complexes, which were then pelleted by centrifugation, washed and counted by gamma counting. Specific IAB binding was calculated by subtracting the NSB counts from the total counts of the corresponding tubes. Specific counts precipitated were converted to µU of insulin based on the specific activity of the radiolabeled insulin used in the assay. Data are presented in FIG. 2 as total IAB binding capacity in µU of insulin bound per ml of serum tested.

Example 18

Insulin-Glycogen Conjugate Behavior In vivo

Figure 3:
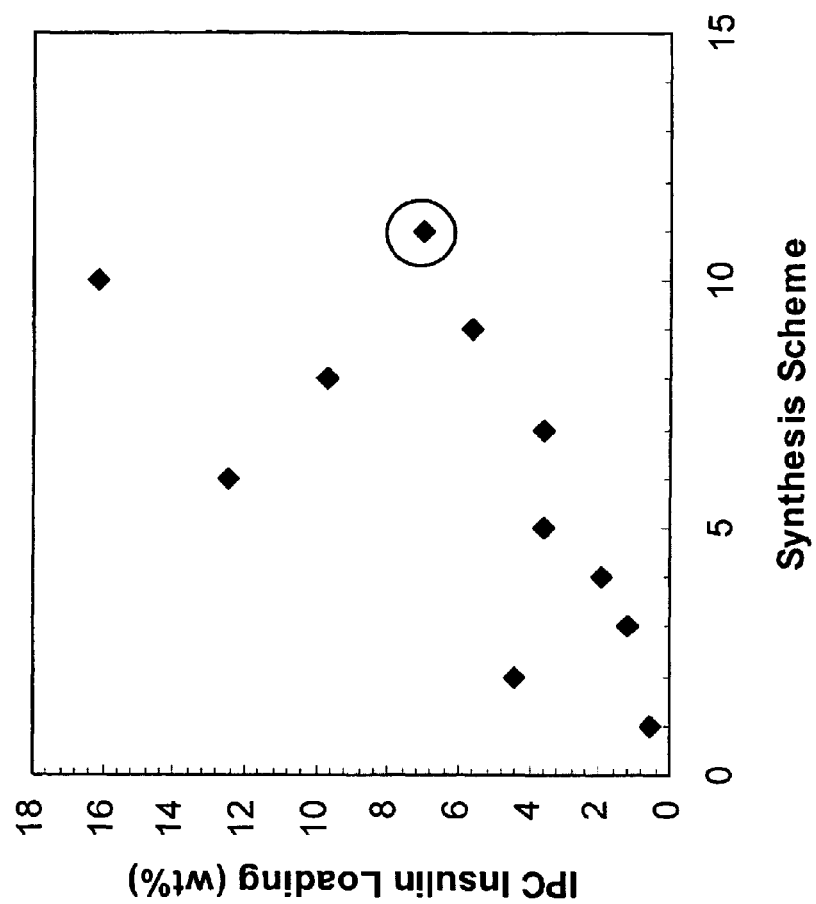
FIG. 3 shows a scatter plot of insulin/conjugate loading w/w % as measured by amino acid analysis for various synthesis schemes arbitrarily delineated 1-10. The circled point corresponds to conjugate used in repeated dosage $HbA_{1c}$ study: 7.0±0.1 wt % insulin/conjugate.

The inventors have demonstrated controllable insulin loadings from 0.5-15% w/w of insulin-glycogen conjugates and found that a 7% w/w loading is suitable for long-term repeated dose studies in STZ-diabetic rats (FIG. 3). As noted previously, other competitive binding applications attempt to release unmodified insulin from a reservoir by trapping a glucose-responsive gel between porous membranes. However, the use of support membranes ultimately leads to a complex system with slow diffusion rates. Consequently, excessively high glucose concentrations (>400 mg/dl) are required to significantly increase insulin diffusion. Furthermore, once glucose is removed from the system, the decrease in insulin release rate lags behind by several hours. In addition, devices such as those based on glucose-responsive membrane-controlled reservoirs will always require maintenance and therefore repeated invasive surgery.

Figure 4:
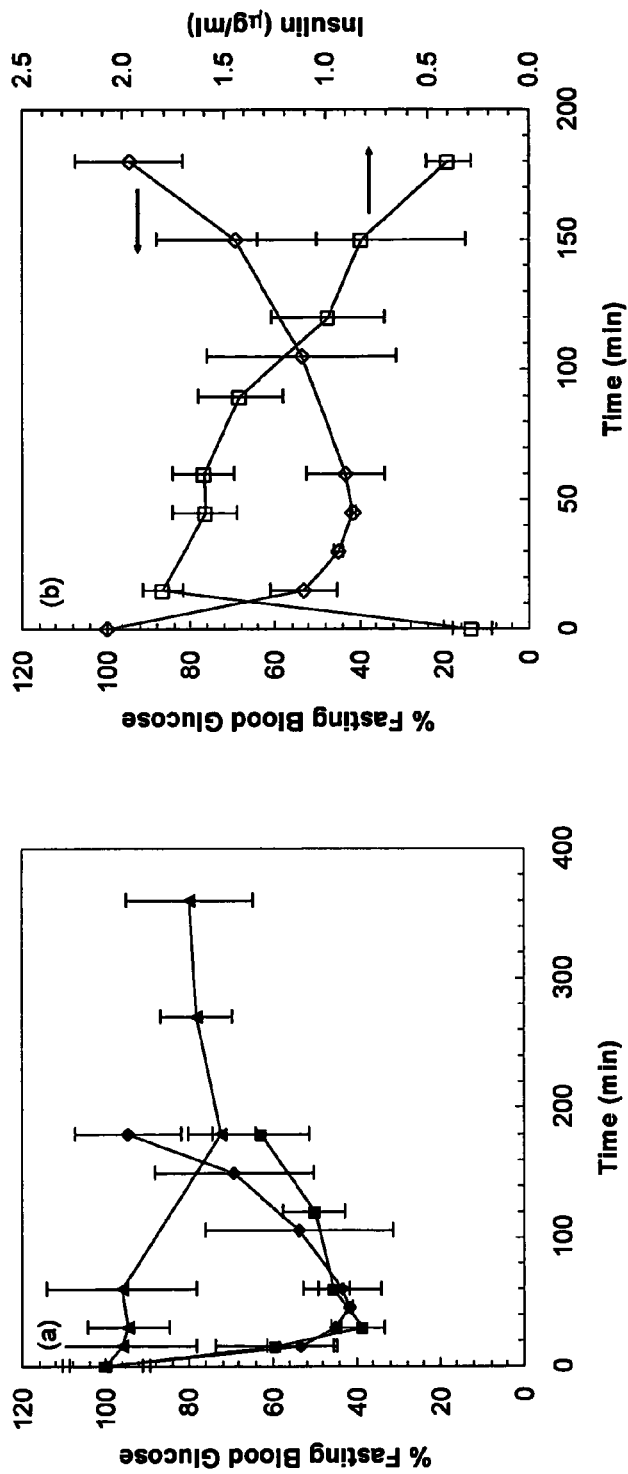
FIG. 4 shows (a) Blood glucose depression profiles in male SD rats (n=3) for subcutaneously injected (▲) insulin-dextran (70 K), (♦) insulin-glycogen (Type II oyster), and (■) unmodified human recombinant insulin. Insulin-polymers were injected at 2.5 U of conjugated insulin/kg; unmodified insulin was injected at 2.0 U/kg. (b) (◇) Blood glucose depression and (□) serum insulin profiles for subcutaneously injected insulin-glycogen at 2.5 U of conjugated insulin/kg. $T_{max}$~15-45 min.; $T_{nadir}$~30-45 min.; and $T_{70\% BGL}$~150 min. Insulin levels were measured using a Porcine Insulin ELISA kit (ALPCO Diagnostics, Windham, N.H.) and blood glucose levels were measured using a Medisense® Precision Xtra™ glucometer.

The in vivo digestion behavior of the insulin-glycogen conjugate was assessed via subcutaneous injection (alone without a glucose-binding molecule such as Con A) into normal male SD rats. As shown in FIG. 4, the times to reach the serum insulin peak ($T_{max}$) and glucose nadir ($T_{nadir}$) concentrations were found to be between 30-45 minutes after injection, serum immunoreactive insulin half-life was less than 120 minutes, and the time to return to within 70% of fasting glucose levels ($T_{70\% BGL}$) was less than 180 minutes. Therefore, despite being chemically bound to a >100,000 kDa polymer, the insulin acts just as rapidly as unconjugated insulin in vivo.

Figure 5:
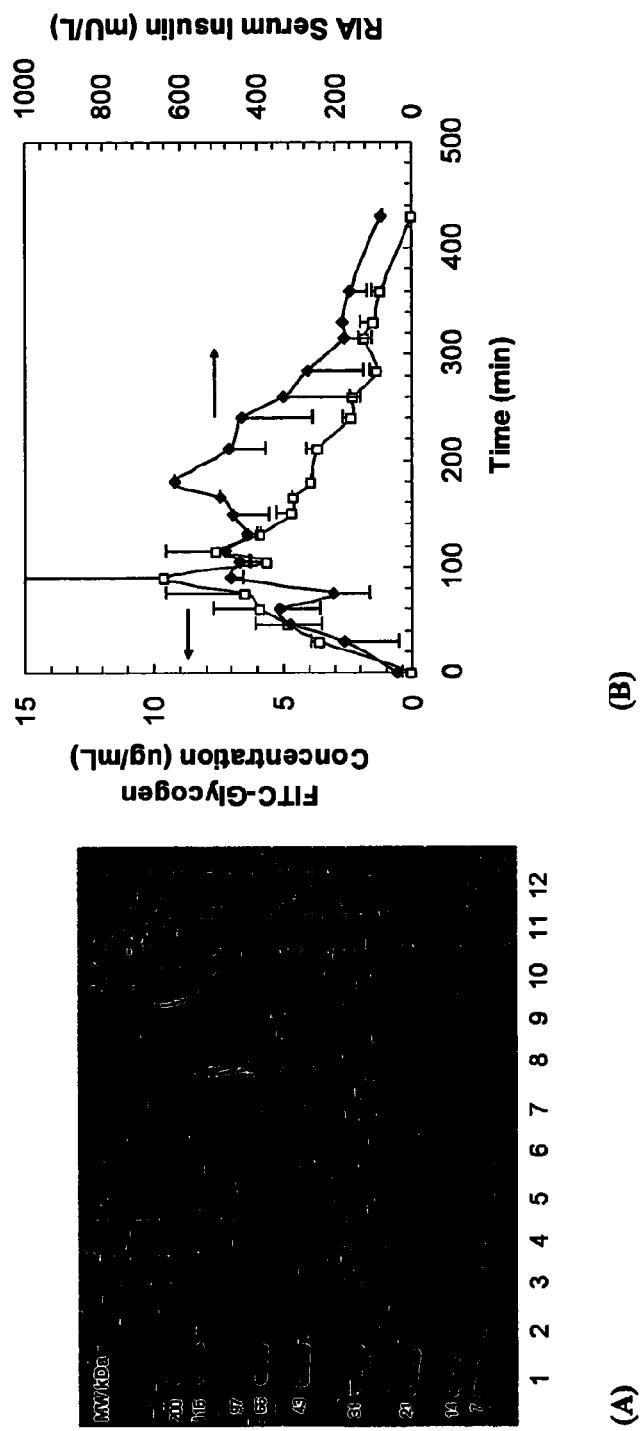
FIG. 5 shows (a) denaturing SDS-PAGE demonstration of the amylase-induced breakdown of intact conjugate into low molecular weight products and insulin. Lanes: (1) MW standards, (2) recombinant insulin at 10 mg/ml, (3) recombinant insulin at 1 mg/ml, (4) intact conjugate at 7% wt. insulin loading, (5) saliva control, (6 through 12) intact conjugate mixed with dilutions of human salivary amylase; dilutions of human saliva are at 1, 4, 16, 64, 128, 256 and 512×, respectively; (b) serum fluorescence and insulin levels for a bolus FITC-conjugate injection at t=0 in normal SD rats (n=2). (□) Serum Fluorescence corresponding to FITC-conjugate absorption and elimination measured at $\square_{ex}$=485 nm and $\square_{em}$=525 nm. (♦) Serum insulin levels (mU/L) as measured by RIA.
Figure 6:
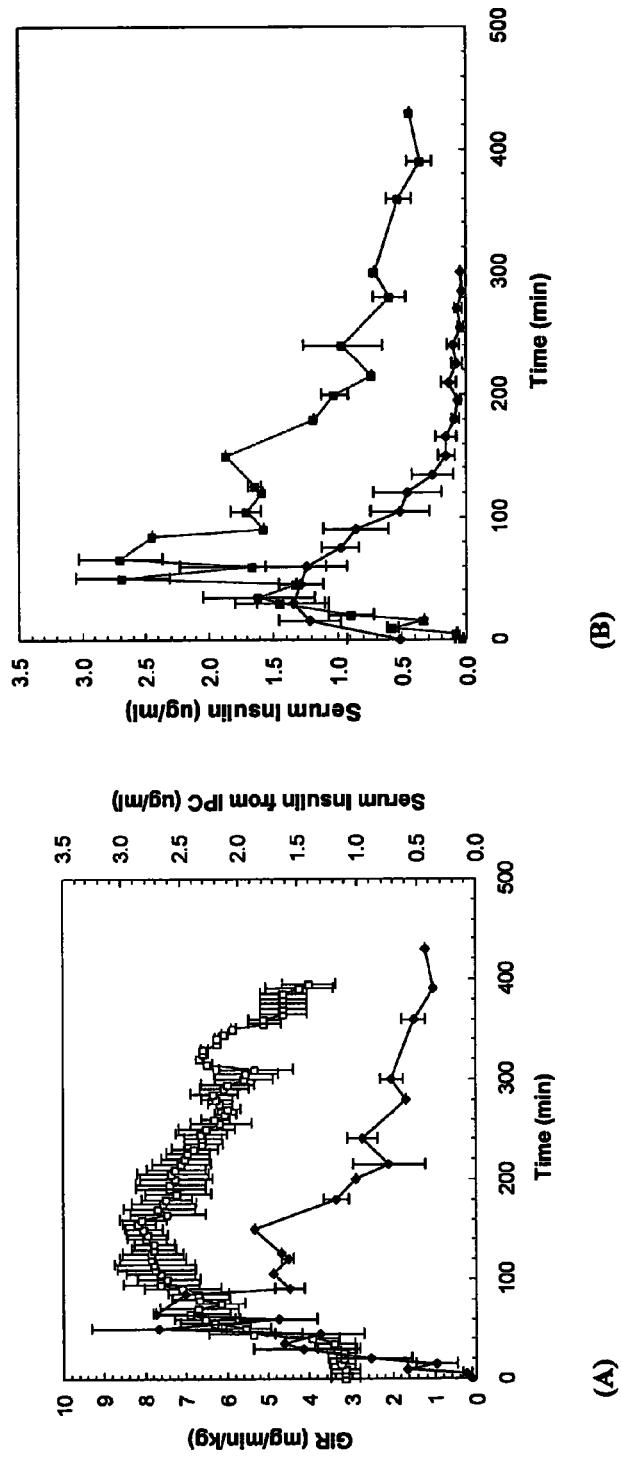
FIG. 6 shows (a) euglycemic glucose clamp results on n=5 normal felines dosed with 0.5 U/kg conjugate, (□) glucose infusion rate (GIR) and (♦) serum insulin concentration as measured by porcine insulin ELISA (ALPCO Diagnostics, Inc., Windham, N.H.) (b) serum insulin concentration versus time for n=5 normal cats dosed with 0.5 U/kg of (♦) human recombinant insulin and (■) IPC.

SDS-PAGE has confirmed that the insulin-glycogen conjugate is essentially free from unconjugated insulin (FIG. 5a). SDS-PAGE on insulin-glycogen incubated with amylase, however, shows an increase in native insulin band intensity and a corresponding decrease in high MW insulin-glycogen band intensity (FIG. 5a). Therefore, unlike insulin-dextran, insulin-glycogen is rapidly degraded by amylases in vitro and in vivo to release bioactive insulin with a MW nearly identical to unmodified insulin, thereby preserving its pharmacological activity. To further illustrate this point, conjugate constructed from FITC-labeled glycogen was injected s.c. at a dose of 12 U/kg into n=2 non-diabetic JV/JV rats and the glucose clamped at 111±23 mg/dl for the following 7 hrs. Serum was collected from the other catheter as a function of time and analyzed for fluorescence (fmax, Molecular Devices, Sunnyvale, Calif.) to determine glycogen absorption rate and insulin levels (RIA, Joslin Diabetes Center). FIG. 5b demonstrates the rapid glycogen absorption and elimination rate and nearly a one-to-one correspondence between serum fluorescence and insulin concentrations. Furthermore, the inventors have also confirmed the conjugate bioactivity in non-diabetic felines using a euglycemic clamp protocol and verified that the amylase degradation-enabled PK/PD parameters hold between species (FIG. 6).

Comparative Example 19

Insulin-Dextran vs. Insulin-Glycogen Conjugates

U.S. Patent Application Publication No. 2004-0202719 to Zion et al. describes insulin-dextran conjugates. These conjugates fail to form insoluble cross-linked gels in the presence of multivalent glucose-binding agents unless the molecular weight (MW) of the dextran component is greater than 70K. However, subcutaneously administered conjugates with dextran MW>70K are very slowly absorbed into the systemic circulation. If the MW is decreased to a sufficiently low value the insulin-dextran conjugate will be absorbed more rapidly, but the system will be soluble (i.e., like the Brownlee system of U.S. Pat. No. 4,348,387). Although Zion et al. make reference to increasing the biological activity of the insulin-dextran conjugate by releasing insulin from a cleavable conjugate, they state that the cleavable conjugate is first absorbed into systemic circulation where it is then rapidly cleaved. Zion et al. do not describe how the high MW insulin-dextran conjugates can be absorbed into systemic circulation prior to cleaving.

This example compares the in vivo pharmacodynamic profiles of subcutaneously administered insulin-glycogen (Oyster Type II, Sigma-Aldrich, MW~1,000K) and insulin-dextran (Sigma-Aldrich, MW~70K). The insulin-glycogen conjugates are more rapidly absorbed than the insulin-dextran conjugates because the former are digested by enzymes at the site of administration.

Insulin-dextran was synthesized using a modified cyanogen bromide (CNBr) coupling reaction. Briefly, 500 mg of dextran (MW=70K, Sigma-Aldrich) was dissolved in 50 ml of deionized water. 56 mg of solid CNBr was added to the resulting solution and the pH was maintained at 10.7±0.2 using 5 N NaOH solution. After stirring for 15 min, another 56 mg of solid CNBr was added and the pH was maintained at 10.7±0.2 while stirring for 45 min. 300 mg of human recombinant insulin was then added to the solution, and the pH was adjusted to 9.15 using solid sodium bicarbonate. The solution was stirred overnight, ultrafiltered exhaustively against DI water using a 10K MWCO polyethersulfone disc membrane filter (Millipore, Bedford, Mass.), and lyophilized. The resulting powder was then purified from unconjugated insulin by high-performance liquid chromatography (Waters, Milford, Mass.) using a 1 M acetic acid mobile phase over a Superdex™ 75 packed column (Amersham Biosciences, Piscataway, N.J.). The insulin-dextran fraction was then lyophilized to obtain the conjugate as a pure powder (InsFITC-Dex70K or InsTRITC-ManDex70K). The degree of insulin conjugation was 10% (w/w) as determined by the method of Example 10.

Subcutaneous injections of insulin-dextran were administered using 0.25 ml of a sterilized 1×PBS solution (0.88 equivalent mg insulin/nil) behind the neck of two fasted normal rat groups (Male Sprague-Dawley, 200-250 g, n=4). Measurements of glucose and insulin values from tail vein blood samples were performed at −15 and 0 minutes, and at 15, 30, 45, 60, 90, 120, 180, 240, 300 and 360 minutes after injection.

As shown in FIG. 4, the times to reach the glucose nadir ($T_{nadir}$) concentration was found to be about 3 h after injection, and the serum glucose levels remain depressed for at least five hours post injection. Therefore, with this type of protracted pharmacodynamic profile, it is difficult to obtain other parameters such as time to return to within 70% of fasting glucose levels ($T_{70\% BGL}$) which one can conclude was at least greater than 2.5 hours. These results are in stark contrast with the results shown on the same graph in FIG. 4 that were obtained under the same conditions with an insulin-glycogen conjugate.

Comparative Example 20

FITC-Polymer Pharmacokinetic Profile

This example reinforces comparative Example 19 by using serum fluorescence measurements to further demonstrate the difference in pharmacokinetic profiles of glycogen (which is rapidly degraded by enzymes) and dextran (which cannot be broken down by enzymes). Each polymer was fluorescently labeled and injected subcutaneously into male SD rats. The concentration of polymer and/or breakdown products absorbed into systemic circulation was determined by measuring the amount of fluorescence in serum as a function of time after the injection.

Fluorescein isothiocyanate glycogen (FITC-glycogen) was synthesized by first preparing a 2 mg/ml solution of glycogen in 0.1 M sodium carbonate buffer (pH 9) and a solution of fluoroscein isothiocyanate (FITC) in anhydrous DMSO at 1 mg/ml. To 1 ml of the glycogen solution, 50 μL of FITC solution was added slowly in 5 μL aliquots under gentle stirring at room temperature. The reaction was then incubated in the dark for 8 hours at 4° C. followed by the addition of $NH_4Cl$ to a final concentration of 50 mM. After another 4° C. incubation for 2 hours, xylene cyanol and glycerol were added to 0.1% and 5%, respectively. Finally, the FITC-glycogen was separated from the reaction medium by ethanol precipitation and centrifugation followed by redissolution in DI water. The FITC-glycogen water solution was then purified 3× by repeated ethanol precipitation and redissolution, followed by lyophilization to obtain the essentially pure powder.

Fluorescein isothiocyanate dextrans of MW 70K, 500K (FITC-Dex-70, FITC-Dex-500) were purchased from Sigma-Aldrich (St. Louis, Mo.) and used without further purification.

Figure 7:
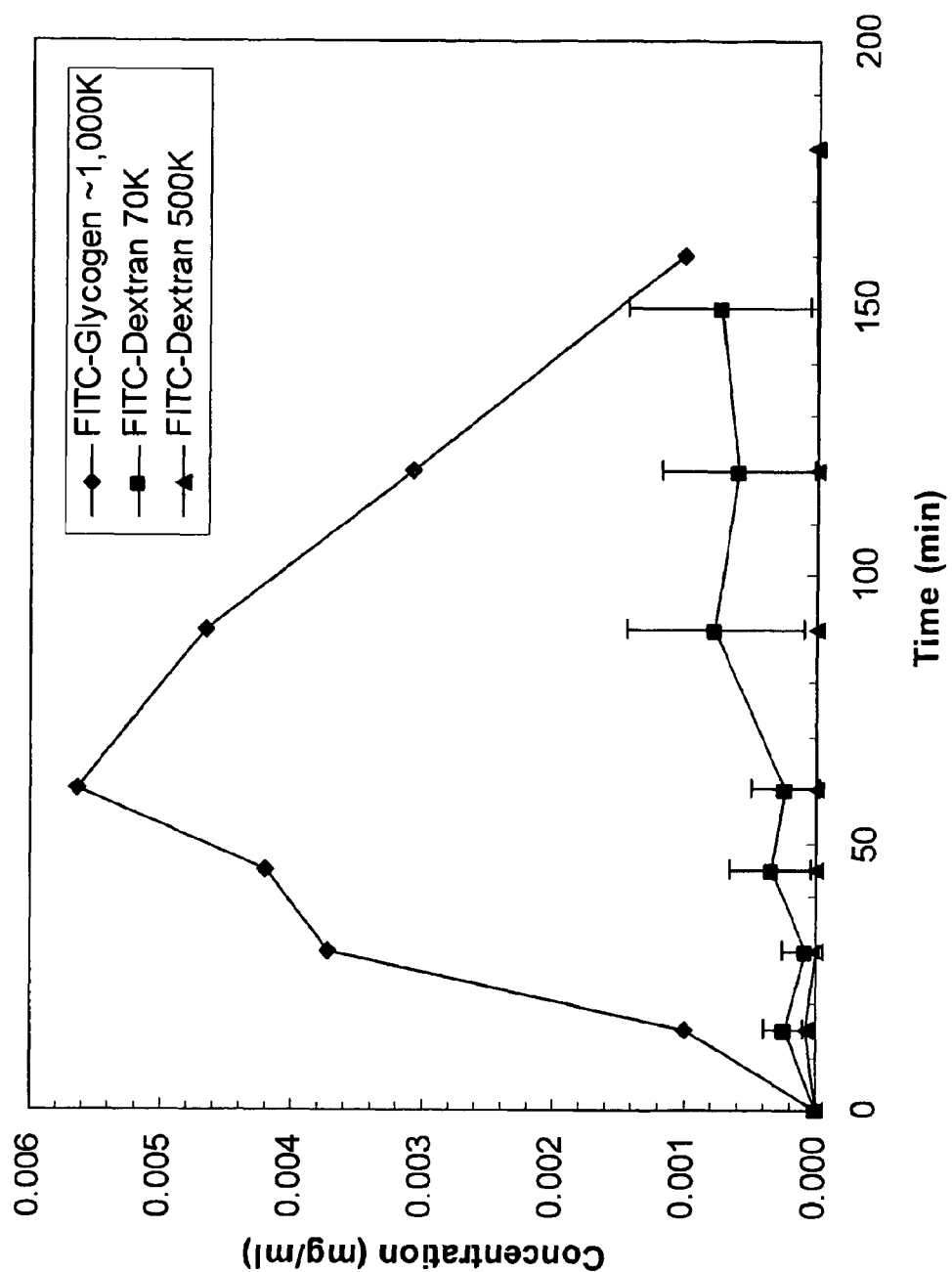
FIG. 7 shows the results of serum fluorescence measurements of FITC labeled glycogen (MW~1,000K) and dextran (MW~70K or 500K).

Each FITC-polymer was dissolved in 1×PBS buffer at 10 mg/ml and injected sub-Q into n=3 rats at time 0. Serum was collected every 15-30 min over the next 3.5 hours and serum fluorescence measured using a fluorescence spectrophotometer plate reader (Fmax, Molecular Devices, Sunnyvale, Calif.) FIG. 7 demonstrates that the rapidly degradable FITC-glycogen, despite having a MW of ~1000K, absorbs significantly faster into systemic circulation than even the FITC-Dex-70 having a MW of 70K, which is non-degradable.

IV. Materials for Controllably Releasing a Conjugate

This fourth set of examples describes the preparation of exemplary materials for controllable releasing conjugates. The examples also describe some of their in vitro and in vivo properties.

Example 21

Insulin-Glycogen Based Hydrogel (I)

This example describes the preparation of an exemplary glucose-sensitive controlled release material from insulin-glycogen conjugates and pegylated Concanavalin A (PEG-Con A).

Insulin-Glycogen Conjugate

The insulin-glycogen conjugate was prepared according to the CDAP coupling method of Example 3 using the insulin and glycogen of Example 1.

Concanavalin A

Concanavalin A (Con A) is a glucose/mannose binding lectin that exists as a tetramer at physiological pH and temperature. Con A was produced via extraction from the jack bean (*Canavalia ensiformis*) by the method of Agrawal and Goldstein (*Biochim. Biophys. Acta* 147:262-271, 1967). Several commercial sources of Con A exist, with one of the largest manufacturers being (EY Labs, San Mateo, Calif.) which can produce between 1 g and 1 kg scales of purified Con A. Typically, the purified Con A received from commercial sources still contains small molecular weight protein impurities that need to be removed before use. These impurities were removed as described by Sophianopoulos and Sophianopoulos (*Prep. Biochem.* 11:413-435, 1981). Briefly, Con A was dissolved at a concentration of 20 mg/ml in 80 mM glycine buffer containing 1.0M sodium chloride, 3 mM of manganese chloride, and 3 mM of calcium chloride at a pH of 3.1. The solution was cooled to 6° C. using an ice bath, and the solution was stirred for 17 hours overnight at 6° C. The next day the solution was warmed to room temperature, followed by heating at 45° C. for 2 hours. Upon cooling the solution was centrifuged at 1500×g for 15 minutes (Allegra 21R, Beckman Coulter, Fullerton, Calif.), and the precipitate was discarded. The supernatant solution was adjusted to a pH of 4.9 using 1M sodium acetate solution, and the supernatant was then ultrafiltered using an Amicon 400 ml cell (Millipore, Bedford, Mass.) equipped with a 25 kDa molecular weight cutoff membrane. Dialysis was carried out using pH 7 distilled water with 0.05 mM calcium chloride and 0.05 mM manganese chloride, after which time the Con A solution was lyophilized to give a nearly salt-free Con A powder that is free of the low molecular weight protein impurities. The final powder purity was confirmed via denaturing polyacrylamide gel electrophoresis (SDS-PAGE), ion exchange chromatography, and circular dichroism (CD) spectroscopy.

Pegylation Reagent

Pegylation reagents consist of poly(ethylene glycol) (PEG) chains attached to a linker group that activates the PEG chains for covalent attachment of proteins through reaction with the ε-amino lysine residues. In this Example, PEG2-NHS-5k was used which has a "V-shaped" structure comprising two 5 kDa molecular weight chains of PEG attached to an NHS ester. The NHS ester is an activated molecule that reacts easily with lysine groups to form a covalent amide linkage. The PEG2-NHS-5k reagent is readily available in 5 g quantities (e.g., from Nektar Therapeutics, San Carlos, Calif.).

Pegylated Con A

Pegylated Con A (PEG-Con A) was prepared by dissolving 500 mg of Con A (EY Labs, San Mateo, Calif.) in 100 ml of a 100 mM borate buffer (pH=10). After dissolution, the contents were heated to 37° C. using a heated water bath and temperature controller. Next, a desired amount of PEG2-NHS-5k (Nektar Therapeutics, San Carlos, Calif.), was dissolved in 7.67 ml of deionized water. The PEGylation agent solution was slowly added dropwise via a pipette to the heated Con A solution. The resulting solution was allowed to react at 37° C. for one hour, after which time the reaction mixture was poured into 300 mL of 150 mM phosphate buffered saline. The solution was then ultrafiltered using a 400 ml Amicon cell (Millipore, Bedford, Mass.), a 50 kDa MWCO membrane (Millipore, Bedford, Mass.), and a pH 7.4 aqueous solution of 0.05 mM calcium chloride and 0.05 mM manganese chloride to remove unreacted PEGylation agent and salts. The ultrafiltered solution was then lyophilized (Freezemobile, Virtis, Gardiner, N.Y.) to give the pure protein as a dry white powder.

Glucose-Sensitive Controlled Release Material

The glucose-sensitive controlled release material was produced using a dual-syringe setup comprising two 1 ml syringes. Briefly, 1 g of purified insulin-glycogen conjugate was dissolved in 20 ml of 200 mM BES buffer, pH 7.4, 150 mM sodium chloride to give a 50 mg/ml conjugate solution. In another vial, 1 g of purified PEG-Con A was dissolved in 10 ml of 20 mM BES buffer, pH 7.4, 0.1 mM manganese chloride, and 0.1 mM calcium chloride to give a 100 mg/ml solution.

Each solution was centrifuged at 5000×g (Allegra 21R, Beckman Coulter, Fullerton, Calif.), and the supernatant was coarse-filtered through a 0.45 μm filter followed by sterile filtration through a 0.22 μm filter. 200 μl of each individual solution was mixed in a sterile centrifuge tube and allowed to react for one hour. The resulting gel was centrifuged and washed exhaustively under aseptic conditions followed by aseptic loading into a 0.5 ml 27G ½" insulin syringe which was then used to administer the gel subcutaneously.

Example 22

Insulin-Glycogen Hydrogel Release Dynamics In vitro

Figure 8:
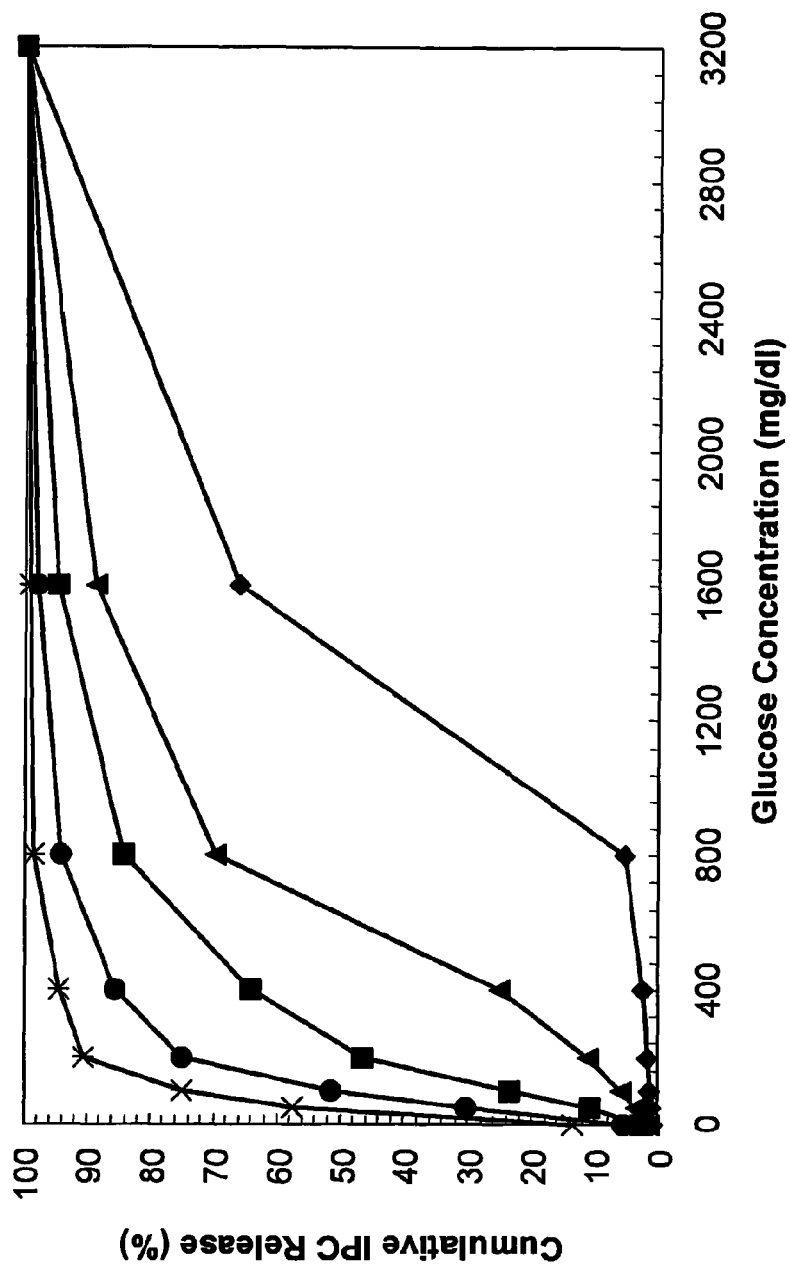
FIG. 8 shows glucose set point (GSP) curves for Con A-insulin-glycogen conjugate gels containing (♦) 0.0, (▲) 0.1, (■) 0.5, (●) 0.9, and (*) 1.0 weight fraction of dimeric, succinylated Con A.

In certain embodiments, the glucose sensitivity of an inventive material (e.g., a material prepared according to the method of Example 21) can be adjusted by modifying the characteristics of its components. Thus, modification of the valency of the multivalent glucose-binding molecule, the degree and MW of PEG modification, the molecular weight or insulin loading of the insulin-glycogen conjugate, and/or substituting glucose units with higher affinity mannose units allows precise adjustment of glucose sensitivity. In this way, the glucose sensitivity can be adjusted from physiologically hypoglycemic to hyperglycemic concentrations (50-500 mg/dl). For example, chemically modified dimeric Con A when mixed at varying ratios with tetrameric Con A effectively shifts the glucose set point (GSP) from over 1,000 mg/dl to under 100 mg/dl (FIG. 8). Manipulation of the glucose setpoint and the loading of the conjugate enables precise tuning of the glucose-responsive insulin release profile.

Figure 9:
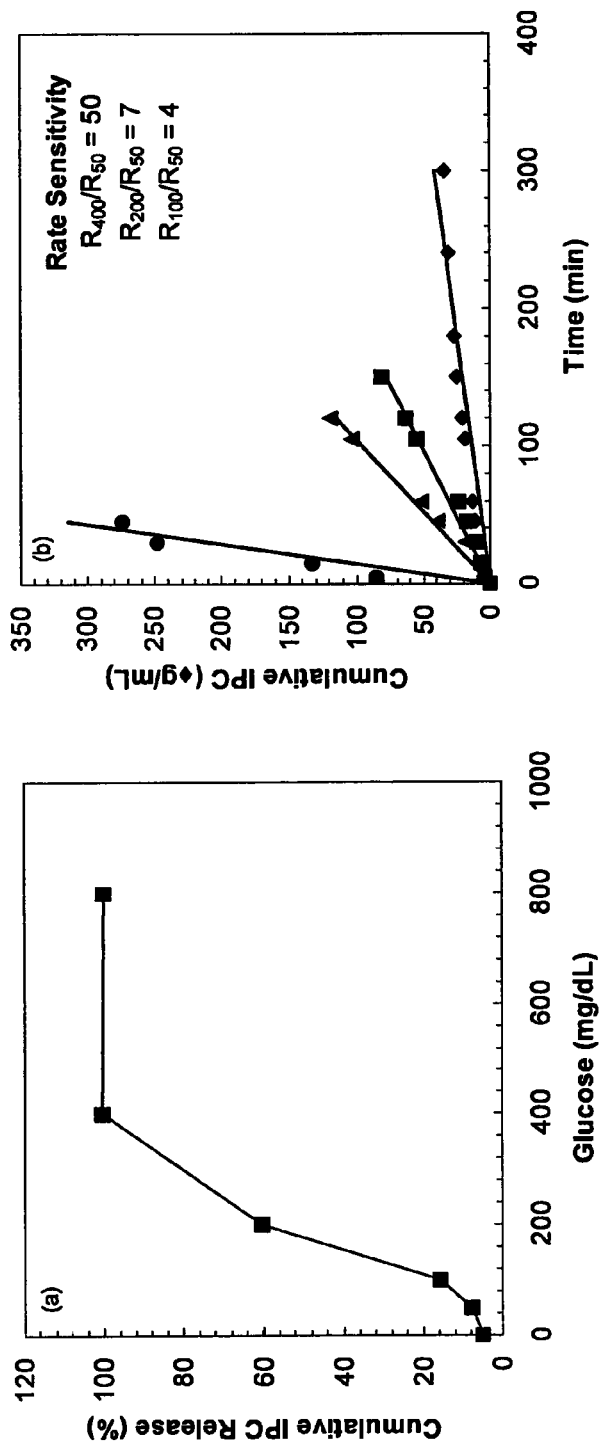
FIG. 9 shows (a) glucose set point (GSP) curve for dimeric Con A-insulin-glycogen gels (insulin loading=0.6% w/w) and (b) corresponding in vitro glucose-responsive release kinetics for glucose concentrations of (♦) 50, (■) 100, (▲) 200, and (●) 400 mg/dl. Inlay: Rate Sensitivity data corresponding to the ratio of pseudo-first order release for a particular glucose concentration ($R_x$, where x=100, 200, and 400 mg/dl) to that obtained at 50 mg/dl ($R_{50}$).

Furthermore, the inventors have correlated the GSP curve (FIG. 9*a*) to in vitro release rates in buffered saline solutions containing varying concentrations of glucose such that the rate of insulin-glycogen release from the gels increases by over a factor of 50, when the glucose concentration increases from 50 to 400 mg/dl (FIG. 9*b*), closely resembling the relative increase in insulin release rate for isolated islet cell cultures.

Figure 10:
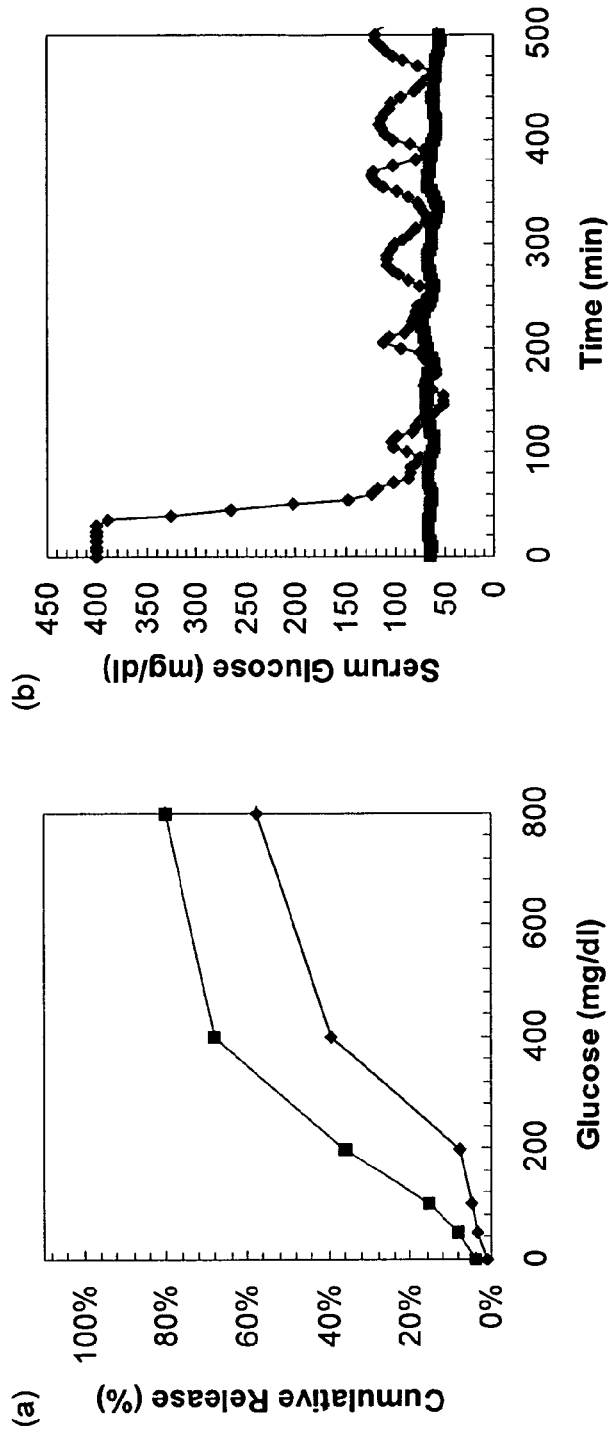
FIG. 10 shows (a) GSP curves for (■) lower set point and (♦) higher set point formulations and (b) corresponding CGS traces in STZ-diabetic rats.

The inventors have also shown how materials with increasingly "leaky" or low glucose set points translate into more hypoglycemia in vivo as measured by CGS on STZ-rats. FIG. 10*a* shows a GSP curve for two different formulations, which were then administered to STZ-diabetic rats by subcutaneous injection and tracked over time by CGS. The higher set point formulation was capable of cycling between 50 and 120 mg/dl while the lower set point formulation pushed the rat into hypoglycemia during the entire duration of the experiment (FIG. 10*b*).

Example 23

Improved Therapeutic Window Compared to Conventional Insulin

Figure 11:
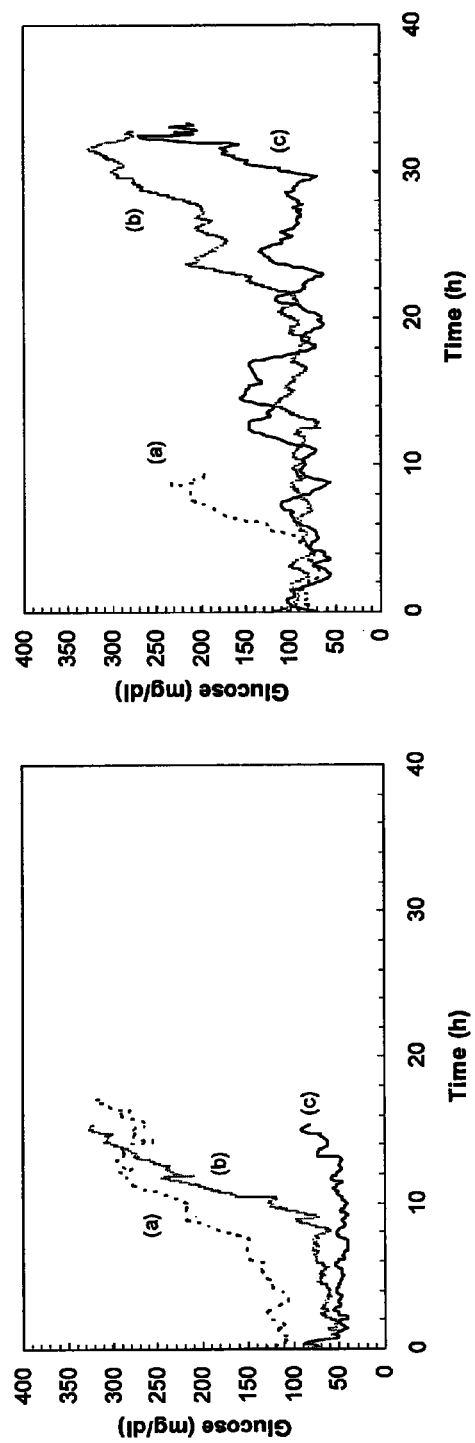
FIG. 11 shows CGS traces for STZ-diabetic rats (n=2 for each group) treated with (left) (a) 10, (b) 20, and (c) 30 U/kg NPH and (right) (a) 50 ul, (b) 150 ul, and (c) 200 ul of a inventive gel formulation.

By virtue of its glucose-responsive kinetics and ability to shut off below a critical glucose concentration, the glucose-sensitive material of Example 21 has a much higher therapeutic window than commercialized long-acting insulins such as insulin NPH (Novolin®ge NPH, Novo Nordisk A/S). Longer glucose control with insulin NPH can only be achieved with larger doses which ultimately lead to more hypoglycemia. FIG. 11 (left) shows continuous glucose sensor (CGS, Guardian RT Wireless, Medtronic Minimed) traces of STZ-rats (60 mg/kg STZ after overnight fast) responding to increasing doses of insulin NPH ((a) 10, (b) 20 and (c) 30 U/kg). The 10 U/kg dose is the only one that does not cause hypoglycemia, but the rats (n=2 for each dose) returned to hyperglycemia several hours later. The highest dose of NPH was active for 18-20 hours but caused hypoglycemia for the entire duration of the experiment. On the other hand, increasing the dosage volume of the glucose-sensitive material of Example 21 extended the duration of control while maintaining normal blood glucose levels (FIG. 11 (right), (a) 50 ul, (b) 150 ul, and (c) 200 ul gel). Most importantly, with just a 200 ul size gel, the inventors were able to control blood glucose levels for over 24 hours without causing hypoglycemia.

Example 24

HbA$_{1c}$ Reduction Over One Week with Minimal Hypoglycemia

Figure 12:
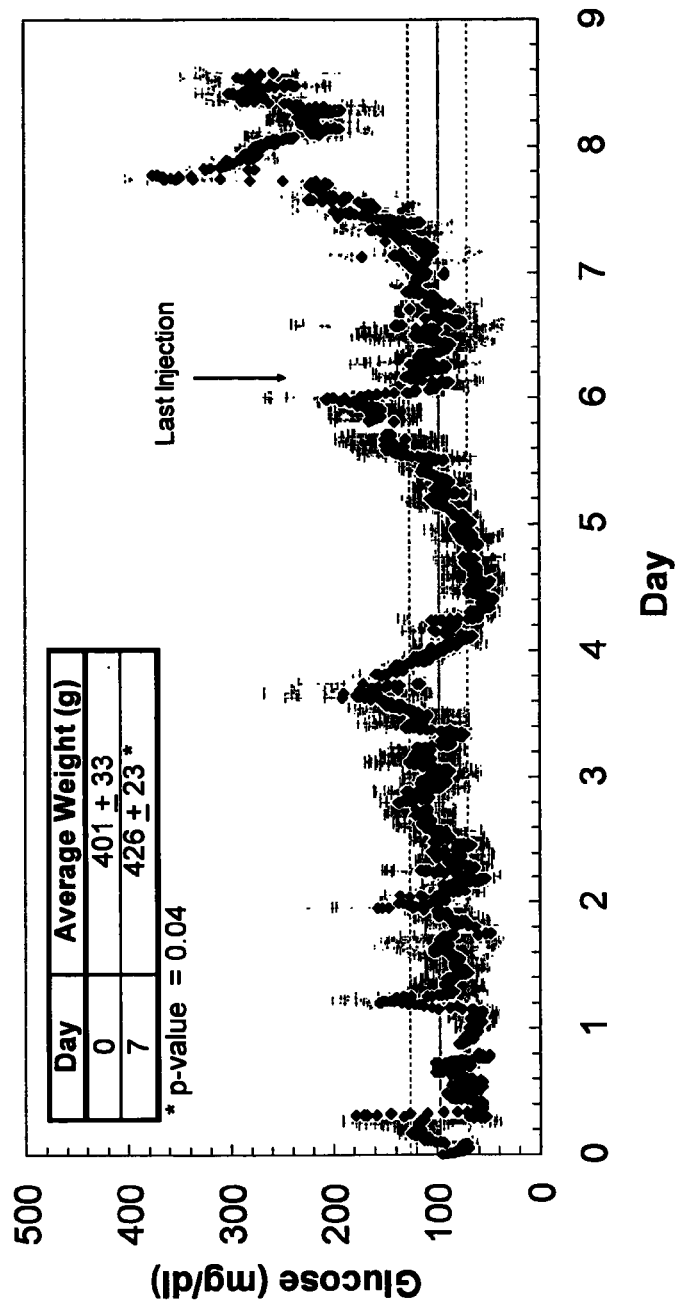
FIG. 12 shows average CGS values for STZ-diabetic rats (n=6) treated with an average daily dose of 150±30 μl of an inventive material. The arrow represents the time of the last gel injection (Day 6 of the study). The average glucose value (solid line) for all six rats from Day 0 to Day 7=98 mg/dl±29 mg/dl (dotted lines). Inlay: Average body weights on day 0 and day 7 demonstrating a statistically significant 6% increase in weight over the study (p<0.05).

The gold-standard for determining the extent of long-term glycemic control is a normalized HbA$_{1c}$ level. Achieving normalized HbA$_{1c}$ values with conventional insulin preparations is nearly impossible without risking frequent hypoglycemia. However, the inventors have been able to reduce HbA$_{1c}$ to near normal levels in STZ-induced diabetic rats (60 mg/kg STZ after overnight fast) with a single daily subcutaneous (s.c.) injection of the glucose-sensitive material of Example 21 while maintaining average blood glucose values at 98±29 mg/dl and causing little to no hypoglycemia (FIG. 12). The arrow in FIG. 12 represents the time of the last gel injection (Day 6 of the study). The average glucose value (solid line, 98 mg/dl) is shown with error ranges (dotted lines, ±29 mg/dl). The inlay to FIG. 12 shows the average body weights on day 0 and day 7 demonstrating a statistically significant 6% increase in weight over the study (p<0.05). One week after STZ-injection, the rats were enrolled on a two-week long daily dose regimen of 30 U/kg NPH and then switched to three weeks of daily dosing of the inventive material. The two weeks of NPH injections did not significantly reduce HbA$_{1c}$ values versus baseline. The first two weeks of dosing with the inventive material were used to determine the optimal volume and glucose set-point for 24-h control. In the final week, the rats were equipped with CGS systems and tracked continuously for the final week (FIG. 12). Rats were dosed at the same time each day with the same formulation except in cases where the gel was found to burn out, in which case a larger volume of the same formulation was administered earlier in the day to return to the same dosing schedule. On average, the rats received 150±30 µl of inventive gel per day. At the end of the final week, the rats had gained weight (FIG. 12) and exhibited HbA$_{1c}$ values that were almost indistinguishable from non-diabetic rats monitored over the same period of time. After the final day 6 injection, the rats were tracked for three more days until they returned to hyperglycemia to demonstrate that spontaneous islet regeneration had not occurred during the treatment.

Example 25

Rapid On/Off Characteristics Via Glucose Clamps

The inventors have developed a method for clamping blood glucose levels in double jugular vein (JV/JV) catheterized rats at a desired value for extended periods of time by infusing a 50% dextrose solution through the catheter line. In this type of experiment two key parameters are followed: (a) the target blood glucose level which is set by design and maintained at a particular level by adjusting (b) the glucose infusion rate (GIR). The diabetic rats do not produce enough endogenous insulin to achieve blood glucose levels below 300 mg/dl even under fasting conditions. Therefore, exogenously administered insulin (NPH or the glucose-sensitive material of Example 21) is required to achieve blood glucose levels below 300 mg/dl. As insulin is delivered during the experiment, the GIR is adjusted to compensate for the glucose-lowering activity of the insulin.

Blood glucose levels were sampled frequently via tail vein bleeding and the glucose infusion rate (GIR) varied to compensate for any drift. Once the GIR was dropped to zero, the NPH dosed rats could not rapidly return to 100 mg/dl, because the insulin delivery rate was too slow. On the other hand, a GIR increase of 4× was observed when rats were dosed with an inventive gel and held at 300 vs. 100 mg/dl, indicating a glucose-responsive increase in insulin delivery rate between the two levels. In addition, unlike the NPH-dosed rats, each time the GIR was dropped to zero, the gel-injected rats were capable of rapidly returning to 100 mg/dl (<30 min), albeit with a slight overshoot. Finally, complete dissolution of the inventive material was observed during the last cycle when the GIR required to maintain glucose levels at 300 mg/dl eventually decreases to zero.

In a separate experiment, three different non-diabetic rats were clamped at 100, 200, and 300 mg/dl glucose, respectively, for 8 hrs. Blood samples were taken through the JV catheter approximately every 60 min, centrifuged to separate cells from serum, and analyzed for insulin content by radio-immunoassay (RIA, Joslin Diabetes Center). The insulin levels were averaged to obtain a steady state serum insulin level as a function of glucose concentration. The insulin levels more than tripled as the glucose concentration was increased from 100 to 300 mg/dl in vivo.

Example 26

Injection Site Compatibility

Figure 13:
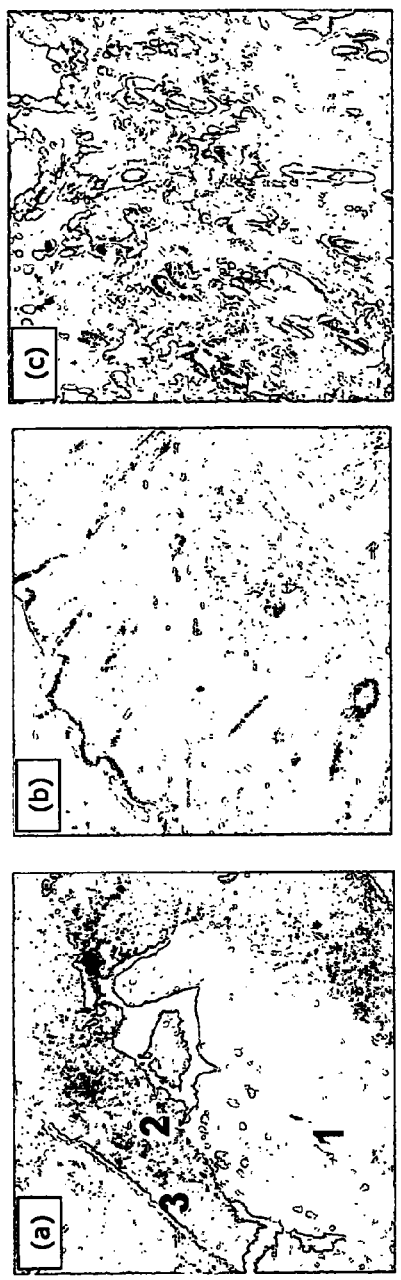
FIG. 13 shows images of tissue samples extracted on Day 3 from the injection site. (a) Con A-gel: Injection site contains (1) an acellular area that is presumably part of the gel; (2) A large region of necrotic neutrophils; and (3) a thick capsule of proliferating fibroblasts, blood capillaries and some macrophages. (b) PEG-Con A-gel: Injection site appears normal with the exception that the muscle layer contained a mild to moderate population of lymphocytes and fewer plasma cells. (c) Saline: Injection site appears normal.

As described in Example 21 and previously, in certain embodiments the multivalent binding agents of an inventive material are chemically modified to reduce undesirable immunogenic reactions. For example, the otherwise mitogenic, inflammogenic, and toxic plant lectin, Con A can be modified with polyethylene glycol (PEG) to prepare a safer multivalent binding agent (PEG-Con A). In vivo histopathology studies have showed that specific PEG-Con A formulations are free from fibrous and necrotic tissue at the injection site with minimal increase in lymphocyte and macrophage local density. Two rats from each group were euthanized on Days 3, 10, and 28. The injection site tissue was excised, fixed in formalin, embedded in paraffin, sectioned and stained with hematoxylin and eosin. The density of fibrous and/or necrotic tissue as well as the presence of granulocytes, macrophages, and lymphocytes were evaluated by a veterinary pathologist. The images of FIG. 13 are images of the tissue samples extracted on Day 3 from the injection site. (a) Con A-gel: Injection site contains (1) an acellular area that is presumably part of the gel; (2) a large region of necrotic neutrophils; and (3) a thick capsule of proliferating fibroblasts, blood capillaries and some macrophages. (b) PEG-Con A-gel: Injection site appears normal with the exception that the muscle layer contained a mild to moderate population of lymphocytes and fewer plasma cells. (c) Saline: Injection site appears normal. Subcutaneous biocompatibility was assessed by injecting the target material (saline, Con A-gel, or PEG-Con A-gel) under the skin of six male SD rats.

Example 27

Formulation of an Injectable, Completely Resorbable Material

The inventive gel of Example 21, has viscosity characteristics that allow easy loading and injection through a standard 27½G insulin syringe obviating the need for invasive surgery. Unlike a device which delivers active components from an inactive, implantable or insertable object, all of the components of the gel are dissolved and exposed to the body at rates that depend on the environmental glucose concentration. This is necessary to avoid unwanted material accumulation after repeated daily dosing. To illustrate this point, gels were synthesized from (i) fluorescently-labeled insulin-glycogen conjugate (FITC-conjugate)/unlabeled Con A and (ii) unlabeled insulin-glycogen conjugate/fluorescently-labeled Con A (FITC-Con A) in the presence of India ink (SpeedBall® Superblack) and injected under the skin of both normal and STZ-diabetic rats on Days 2, 1, and 0 in order to simultaneously observe the injection site post-mortem and monitor the rate of disappearance of each of the components by fluorescence imaging.

The insulin-glycogen conjugate was completely eliminated from the injection site in STZ-diabetic rats both one and two days after injection but still remained at the injection site after one day in normal rats. Taken together, not only is the insulin-glycogen conjugate removed completely from the injection site, its rate of disappearance is dependent on the glycemic state of the animal (i.e. hyperglycemia leads to more rapid elimination of material from the site). Similarly, the FITC-Con A was completely eliminated two days after injection in the STZ-diabetic rats but remained even after two days in the normal rats.

Example 28

Insulin-Glycogen Based Hydrogel (II)

This example describes the preparation of another exemplary glucose-sensitive controlled release material from insulin-glycogen conjugates and succinylated-Concanavalin A (s-Con A). Briefly, 0.100 ml of a 50 mg/ml insulin-glycogen conjugate solution (prepared according to the method of Example 3, using Type II oyster glycogen from and containing 1 wt % insulin) in 200 mM pH 7.4 BES buffer containing 1 mM $CaCl_2$ and $MnCl_2$ was mixed with 0.100 ml of a 100 mg/ml succinylated-Concanavalin A solution (EY Labs, San Mateo, Calif.) in 20 mM pH 7.4 BES buffer containing 1M NaCl, 1 mM $CaCl_2$ and $MnCl_2$. The two solutions were mixed together in a centrifuge tube and allowed to gel. The resulting gel was centrifuged and washed exhaustively to remove any uncrosslinked insulin-glycogen and s-Con A.

1.0 ml of 1×PBS containing 0 mg/dl of D-glucose was added to one of the twenty-four 3 ml wells of a Multiwell™ plate (Becton Dickinson, Franklin Lakes, N.J.). The gel was then added to the solution and agitated for 1 hr using a microplate incubator/shaker ("Jitterbug," Boekel Industries, Philadelphia, Pa.) set at 37° C. After 1 hr, 0.5 ml of release medium was removed and the insulin-glycogen concentration determined by ELISA (ALPCO Diagnostics, Windham, N.H.). The release medium was supplemented with 0.5 ml of a 100 mg/dl glucose solution in 1×PBS to make a 50 mg/dl solution, and the gels were agitated for another hour. This process was repeated for release media with glucose concentrations of 100, 200, 400, and 800 mg/dl for a total of 6 concentrations over 6 hr. The percent insulin-glycogen dissolution was then calculated by normalizing the cumulative concentration of insulin in the release medium as measured by ELISA by that released at 100% gel dissolution. In all cases, 100% dissolution was obtained after the 800 mg/dl glucose incubation.

Other Embodiments

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

We claim:

1. A method for controllably releasing a conjugate within subcutaneous tissue in response to the local concentration of an indicator comprising subcutaneously administering, to a patient in need thereof, a material that comprises:
    a plurality of conjugates that each include a drug covalently linked to a polymer that is a polysaccharide that includes repeating chains of 1,4-linked alpha-D-glucose residues or the polymer is covalently linked to said drug via a spacer that includes a plurality of 1,4-linked alpha-D- glucose residues, wherein said conjugates are susceptible to digestion by an enzyme present in the extracellular space of subcutaneous tissue; and a plurality of multivalent cross-linking agents each containing two or more cross-link receptors, wherein said conjugates are cross-linked by said multivalent cross-linking agents through interactions between the indicator analogs and the cross-link receptors, wherein said interactions are competitively disrupted if an amount of the indicator is present, and wherein competitive disruption of the interactions between the indicator analogs and the cross-link receptors causes the material to release the conjugate in a manner that is dependent on the local concentration of the indicator.

2. The method of claim 1, wherein the material is an insoluble hydrogel.

3. The method of claim 1, wherein the drug is an antidiabetic agent.

4. The method of claim 3, wherein the antidiabetic agent is selected from the group consisting of insulin, insulin analogues, insulin secretagogues and insulin sensitizers.

5. The method of claim 4, wherein the antidiabetic agent is insulin.

6. The method of claim 1, wherein the indicator analog has essentially the same composition as the indicator.

7. The method of claim 1, wherein the indicator is glucose and the drug is an antidiabetic agent.

8. The method of claim 1, wherein the multivalent cross-linking agent is a multivalent glucose-binding molecule.

9. The method of claim 1, the multivalent cross-linking agent is selected from the group consisting of concanavalin A (Con A), succinylated Con A, Con A covalently modified with a polyethylene glycol, and succinylated Con A covalently modified with a polyethylene glycol.

10. The method of claim 1, wherein the indicator is glucose and the indicator analog is glucose or a derivative thereof.

11. The method of claim 1, wherein the indicator is glucose and the indicator analog is mannose or a mannose-containing sugar.

12. The method of claim 1, wherein the material is dissolved in a biocompatible aqueous solution and the solution is injected subcutaneously.

13. A method for treating diabetes comprising subcutaneously administering to a patient in need thereof, a material that comprises:

a plurality of conjugates that each include an antidiabetic agent covalently linked to a polymer that is a polysaccharide that includes repeating chains of 1,4-linked alpha-D-glucose residues or the polymer is covalently linked to said drug via a spacer that includes a plurality of 1,4-linked alpha-D-glucose residues, wherein said conjugates are susceptible to digestion by an enzyme present in the extracellular space of subcutaneous tissue;

a plurality of multivalent cross-linking agents each comprising containing two or more cross-link receptors, wherein said conjugates are cross-linked by said multivalent cross-linking agents through interactions between the glucose analogs and the cross-link receptors, wherein said interactions are competitively disrupted if an amount of glucose is present, and wherein competitive disruption of the interactions between the glucose analogs and the cross-link receptors causes the material to release the conjugate in a manner that is dependent on the local concentration of glucose.

14. The method of claim 13, wherein the material is an insoluble hydrogel.

15. The method of claim 13, wherein the multivalent cross-linking agent is a multivalent glucose-binding molecule.

16. The method of claim 13, wherein the multivalent cross-linking agent is selected from the group consisting of concanavalin A (Con A), succinylated Con A, Con A covalently modified with a polyethylene glycol, and succinylated Con A covalently modified with a polyethylene glycol.

17. The method of claim 16, wherein the multivalent glucose-binding molecule is Con A covalently modified with a polyethylene glycol.

* * * * *